(12) United States Patent
Fuganti et al.

(10) Patent No.: US 10,894,964 B2
(45) Date of Patent: Jan. 19, 2021

(54) USE OF AT(N) INSERTIONS IN PROMOTER ELEMENTS FOR CONTROLLING THE EXPRESSION LEVELS OF CODING SEQUENCES IN PLANTS

(75) Inventors: Renata Fuganti, Londrina (BR); Alexandre Lima Nepomuceno, Londrina (BR); Francismar Correa Marcelino, Londrina (BR); Joao Flavio Veloso Silva, Londrina (BR); Silvana Regina Rochenbach Marin, Londrina (BR); Cesar Augusto Silveira, Londrina (BR); Eliseu Binneck, Londrina (BR)

(73) Assignee: EMPRESA BRASILEIRA DE PESQUISA AGROPECUARIA - EMBRAPA, Brazilia (BR)

( * ) Notice: Subject to any disclaimer, the term of this patent is extended or adjusted under 35 U.S.C. 154(b) by 280 days.

(21) Appl. No.: 13/132,006

(22) PCT Filed: Nov. 28, 2008

(86) PCT No.: PCT/BR2008/000361
§ 371 (c)(1),
(2), (4) Date: Jan. 23, 2012

(87) PCT Pub. No.: WO2010/060162
PCT Pub. Date: Jun. 3, 2010

(65) Prior Publication Data
US 2014/0075594 A1    Mar. 13, 2014

(51) Int. Cl.
*C12N 15/82* (2006.01)
*C07K 14/415* (2006.01)

(52) U.S. Cl.
CPC ........ *C12N 15/8285* (2013.01); *C07K 14/415* (2013.01); *C12N 15/8216* (2013.01); *C12N 15/8237* (2013.01); *C12N 15/8239* (2013.01); *C12N 15/8271* (2013.01); *C12N 15/8273* (2013.01); *Y02A 40/146* (2018.01)

(58) Field of Classification Search
CPC ................. C12N 15/8239; C12N 15/8285
USPC ........................... 536/24.1; 800/279
See application file for complete search history.

(56) References Cited

U.S. PATENT DOCUMENTS 7,126,041 B1    10/2006    Helmer et al.
2005/0155114 A1    7/2005    Hinchey

FOREIGN PATENT DOCUMENTS

EP    1 452 596 A1    9/2004
WO    2005/019408 A2    3/2005

OTHER PUBLICATIONS

International Search Report for PCT/BR2008/000361 dated Jul. 16, 2009.

*Primary Examiner* — Li Zheng
(74) *Attorney, Agent, or Firm* — Sughrue Mion, PLLC

(57) ABSTRACT

The present invention refers to the use of AT(n) insertions in promoter elements for controlling the expression levels of coding sequences in plants. The expression levels of the heat shock protein (Gmhsp17.6-L), when compared in resistant and susceptible individuals in the population, demonstrated that the largest expression levels per quantitative PCR were present in the individuals that contained the largest AT insertions in the promoter region. The invention also refers to gene expression cassettes containing promoter regions of the gene with different numbers of AT insertions fused to the GUS protein, for transforming soybean embryos.

13 Claims, 19 Drawing Sheets
(2 of 19 Drawing Sheet(s) Filed in Color)
Specification includes a Sequence Listing.

FIGURE 2

```
  1   GAATTCTGAA ATTGGGTCTT TTTGTGGGCA CTTTTTGATG TTTTTGTTTA AGTTACTGTA
      CTTAAGACTT TAACCCAGAA AAACACCCGT GAAAAACTAC AAAAACAAAT TCAATGACAT

61   CTGTGGGCCA CAAAACGTAT AGATCAAAGT AGTAATAATA ATATTGATTA AATGATATAT
      GACACCCGGT GTTTTGCATA TCTAGTTTCA TCATTATTAT TATAACTAAT TTACTATATA

121   ATATATATAT ATATATATAT ATATCTAGAA GGTTGTAGAA GACTAGCTAG AACGTACGTA
      TATATATATA TATATATATA TATAGATCTT CCAACATCTT CTGATCGATC TTGCATGCAT

181   TTCGTGTGGA GAAGTCCTGA AGTTTATCGA ATCATCTAAA ACTGCTAAAA TAGCAAACAA
      AAGCACACCT CTTCAGGACT TCAAATAGCT TAGTAGATTT TGACGATTTT ATCGTTTGTT

241   CATTATATTG TAAACAATAT TTTTCTGGAA CATACAAGAG TATCCTTTCA CTTCCTTTAA
      GTAATATAAC ATTTGTTATA AAAAGACCTT GTATGTTCTC ATAGGAAAGT GAAGGAAATT

301   ATACCTCGAG TGTCCCCATT GACATCATCA AACAAGAGAA GAGTTACAGA ATTTCCTGTT
      TATGGAGCTC ACAGGGGTAA CTGTAGTAGT TTGTTCTCTT CTCAATGTCT TAAAGGACAA

361   TACGATCTCA TTACAATTTT GCAACTTTCA AAGCTTATTA GCTAAAGTAA CATCAAAAGA
      ATGCTAGAGT AATGTTAAAA CGTTGAAAGT TTCGAATAAT CGATTTCATT GTAGTTTTCT

421   TGTCATTGAT TCCAAGTATT TTCGGTGGCC CAAGGAGCAA CGTGTTCGAT CCATTCTCAC
      ACAGTAACTA AGGTTCATAA AAGCCACCGG GTTCCTCGTT GCACAAGCTA GGTAAGAGTG

481   TCGATATGTG GGATCCCTTC AAGGATTTTC ATGTTCCCAC TTCTTCTGTT TCTGCTGAAA
      AGCTATACAC CCTAGGGAAG TTCCTAAAAG TACAAGGGTG AAGAAGACAA AGACGACTTT

541   ATTCTGCATT TGTGAACACA CGTGTGGATT GGAAGGAGAC CCAAGAGGCA CACGTGCTCA
      TAAGACGTAA ACACTTGTGT GCACACCTAA CCTTCCTCTG GGTTCTCCGT GTGCACGAGT

601   AGGCTGATAT TCCAGGGCTG AAGAAAGAGG AAGTGAAGGT TCAGATTGAA GATGATAGGG
      TCCGACTATA AGGTCCCGAC TTCTTTCTCC TTCACTTCCA AGTCTAACTT CTACTATCCC

661   TTCTTCAGAT TAGCGGAGAG AGGAACGTTG AGAAGGAAGA CAAGAACGAC ACGTGGCATC
      AAGAAGTCTA ATCGCCTCTC TCCTTGCAAC TCTTCCTTCT GTTCTTGCTG TGCACCGTAG

721   GCGTGGACCG TAGCAGTGGA AAGTTCATGA GAAGGTTCAG ATTGCCAGAG AATGCAAAAG
      CGCACCTGGC ATCGTCACCT TTCAAGTACT CTTCCAAGTC TAACGGTCTC TTACGTTTTC

781   TGGAGCAAGT AAAGGCTTGT ATGGAAAATG GGGTTCTCAC TGTTACTATT CCAAAGGAAG
      ACCTCGTTCA TTTCCGAACA TACCTTTTAC CCCAAGAGTG ACAATGATAA GGTTTCCTTC

841   AGGTTAAGAA GTCTGATGTT AAGCCTATAG AAATCTCTGG TTAAACTTGG TTTCACTGAA
      TCCAATTCTT CAGACTACAA TTCGGATATC TTTAGAGACC AATTTGAACC AAAGTGACTT
```

FIGURE 3

```
  1   GAATTCTGAA ATTGGGTCTT TTTGTGGGCA CTTTTTGATG TTTTTGTTTA AGTTACTGTA
      CTTAAGACTT TAACCCAGAA AAACACCCGT GAAAAACTAC AAAAACAAAT TCAATGACAT

61   CTGTGGGCCA CAAAACGTAT AGATCAAAGT AGTAATAATA ATATTGATTA AATGATATAT
      GACACCCGGT GTTTTGCATA TCTAGTTTCA TCATTATTAT TATAACTAAT TTACTATATA

121   ATATATATAT ATATATATAT ATATCTAGAA GGTTGTAGAA GACTAGCTAG AACGTACGTA
      TATATATATA TATATATATA TATAGATCTT CCAACATCTT CTGATCGATC TTGCATGCAT

181   TTCGTGTGGA GAAGTCCTGA AGTTTATCGA ATCATCTAAA ACTGCTAAAA TAGCAAACAA
      AAGCACACCT CTTCAGGACT TCAAATAGCT TAGTAGATTT TGACGATTTT ATCGTTTGTT

241   CATTATATTG TAAACAATAT TTTTCTGGAA CATACAAGAG TATCCTTTCA CTTCCTTTAA
      GTAATATAAC ATTTGTTATA AAAAGACCTT GTATGTTCTC ATAGGAAAGT GAAGGAAATT

301   ATACCTCGAG TGTCCCCATT GACATCATCA AACAAGAGAA GAGTTACAGA ATTTCCTGTT
      TATGGAGCTC ACAGGGGTAA CTGTAGTAGT TTGTTCTCTT CTCAATGTCT TAAAGGACAA

361   TACGATCTCA TTACAATTTT GCAACTTTCA AAGCTTATTA GCTAAAGTAA CATCAAAAGA
      ATGCTAGAGT AATGTTAAAA CGTTGAAAGT TTCGAATAAT CGATTTCATT GTAGTTTTCT

421   TGTCATTGAT TCCAAGTATT TTCGGTGGCC CAAGGAGCAA CGTGTTCGAT CCATTCTCAC
      ACAGTAACTA AGGTTCATAA AAGCCACCGG GTTCCTCGTT GCACAAGCTA GGTAAGAGTG

481   TCGATATGTG GGATCCCTTC AAGGATTTTC ATGTTCCCAC TTCTTCTGTT TCTGCTGAAA
      AGCTATACAC CCTAGGGAAG TTCCTAAAAG TACAAGGGTG AAGAAGACAA AGACGACTTT

541   ATTCTGCATT TGTGAACACA CGTGTGGATT GGAAGGAGAC CCAAGAGGCA CACGTGCTCA
      TAAGACGTAA ACACTTGTGT GCACACCTAA CCTTCCTCTG GGTTCTCCGT GTGCACGAGT

601   AGGCTGATAT TCCAGGGCTG AAGAAAGAGG AAGTGAAGGT TCAGATTGAA GATGATAGGG
      TCCGACTATA AGGTCCCGAC TTCTTTCTCC TTCACTTCCA AGTCTAACTT CTACTATCCC

661   TTCTTCAGAT TAGCGGAGAG AGGAACGTTG AGAAGGAAGA CAAGAACGAC ACGTGGCATC
      AAGAAGTCTA ATCGCCTCTC TCCTTGCAAC TCTTCCTTCT GTTCTTGCTG TGCACCGTAG

721   GCGTGGACCG TAGCAGTGGA AAGTTCATGA GAAGGTTCAG ATTGCCAGAG AATGCAAAAG
      CGCACCTGGC ATCGTCACCT TTCAAGTACT CTTCCAAGTC TAACGGTCTC TTACGTTTTC

781   TGGAGCAAGT AAAGGCTTGT ATGGAAAATG GGGTTCTCAC TGTTACTATT CCAAAGGAAG
      ACCTCGTTCA TTTCCGAACA TACCTTTTAC CCCAAGAGTG ACAATGATAA GGTTTCCTTC

841   AGGTTAAGAA GTCTGATGTT AAGCCTATAG AAATCTCTGG TTAAACTTGG TTTCACTGAA
      TCCAATTCTT CAGACTACAA TTCGGATATC TTTAGAGACC AATTTGAACC AAAGTGACTT
```

```
SOYHSP176_M11317.1        ATCATCAAACAAGAGAAGAGTTACAGAATTTCCTGTTTACGATCTCATTACAATTTT
GmHSP_17.6-L_BRS133       ATCATCAAACAAGAGAAGAGTTACAGAATTTCCTGTTTACGATCTTATTGCAATTTT
GmHSP_17.6-L_PI595099     ATCATCAAACAAGAGAAGAGTTACAGAATTTCCTGTTTACGATCTCATTACAATTTT
GmHSP_17.6-L_256-S        ATCATCAAACAAGAGAAGAGTTACAGAATTTCCTGTTTACGATCTTATTGCAATTTT
GmHSP_17.6-L_259-S        ATCATCAAACAAGAGAAGAGTTACAGAATTTCCTGTTTACGATCTCATTACAATTTT
GmHSP_17.6-L_266-S        ATCATCAAACAAGAGAAGAGTTACAGAATTTCCTGTTTACGATCTTATTGCAATTTT
GmHSP_17.6-L_JF7002       ATCATCAAACAAGAGAAGAGTTACAGAATTTCCTGTTTACGATCTCATTACAATTTT
GmHSP_17.6-L_JF7027       ATCATCAAACAAGAGAAGAGTTACAGAATTTCCTGTTTACGATCTCATTACAATTTT
GmHSP_17.6-L_JF7056       ATCATCAAACAAGAGAAGAGTTACAGAATTTCCTGTTTACGATCTCATTACAATTTT

SOYHSP176_M11317.1        GCAACTTTCAAAGCTTATTAGCTAAAGTAACATCAAAAGATG
GmHSP_17.6-L_BRS133       GCAACTTTCAAAGCTTATTAGCTAAAGTAACATCAAAAGATG
GmHSP_17.6-L_PI595099     GCAACTTTCAAAGCTTATTAGCTAAAGTAACATCAAAAGATG
GmHSP_17.6-L_256-S        GCAACTTTCAAAGCTTATTAGCTAAAGTAACATCAAAAGATG
GmHSP_17.6-L_259-S        GCAACTTTCAAAGCTTATTAGCTAAAGTAACATCAAAAGATG
GmHSP_17.6-L_266-S        GCAACTTTCAAAGCTTATTAGCTAAAGTAACATCAAAAGATG
GmHSP_17.6-L_JF7002       GCAACTTTCAAAGCTTATTAGCTAAAGTAACATCAAAAGATG
GmHSP_17.6-L_JF7027       GCAACTTTCAAAGCTTATTAGCTAAAGTAACATCAAAAGATG
GmHSP_17.6-L_JF7056       GCAACTTTCAAAGCTTATTAGCTAAAGTAACATCAAAAGATG
```

FIGURE 8

```
SOYHSP176_M11317.1      ATGTCATTGATTCCAAGTATTTTCGGTGGCCCAAGGAGCAACGTGTTCGATCCATT
GmHSP_17.6-L_BRS133_    ATGTCATTGATTCCAAGTATTTTCGGTGGCCCAAGGAGCAACGTGTTCGATCCATT
GmHSP_17.6-L_PI595099   ATGTCATTGATTCCAAGTATTTTCGGTGGCCCAAGGAGCAACGTGTTCGATCCATT
GmHSP_17.6-L_256-S_     ATGTCATTGATTCCAAGTATTTTCGGTGGCCCAAGGAGCAACGTGTTCGATCCATT
GmHSP_17.6-L_259-S_     ATGTCATTGATTCCAAGTATTTTCGGTGGCCCAAGGAGCAACGTGTTCGATCCATT
GmHSP_17.6-L_266-S_     ATGTCATTGATTCCAAGTATTTTCGGTGGCCCAAGGAGCAACGTGTTCGATCCATT
GmHSP_17.6-L_JF7002_    ATGTCATTGATTCCAAGTATTTTCGGTGGCCCAAGGAGCAACGTGTTCGATCCATT
GmHSP_17.6-L_JF7027_    ATGTCATTGATTCCAAGTATCTTCGGTGGCCCAAGGAGCAACGTGTTCGATCCATT
GmHSP_17.6-L_JF7056     ATGTCATTGATTCCAAGTATTTTCGGTGGCCCAAGGAGCAACGTGTTCGATCCATT

SOYHSP176_M11317.1      CTCACTCGATATGTGGGATCCCTTCAAGGATTTTCATGTTCCCACTTCTTCTGTTT
GmHSP_17.6-L_BRS133_    CTCACTCGATATGTGGGATCCCTTCAAGGATTTTCATGTTCCCACTTCTTCTGTTT
GmHSP_17.6-L_PI595099   CTCACTCGATATGTGGGATCCCTTCAAGGATTTTCATGTTCCCACTTCTTCTGTTT
GmHSP_17.6-L_256-S_     CTCACTCGATATGTGGGATCCCTTCAAGGATTTTCATGTTCCCACTTCTTCTGTTT
GmHSP_17.6-L_259-S_     CTCACTCGATATGTGGGATCCCTTCAAGGATTTTCATGTTCCCACTTCTTCTGTTT
GmHSP_17.6-L_266-S_     CTCACTCGATATGTGGGATCCCTTCAAGGATTTTCATGTTCCCACTTCTTCTGTTT
GmHSP_17.6-L_JF7002_    CTCACTCGATATGTGGGATCCCTTCAAGGATTTTCATGTTCCCACTTCTTCTGTTT
GmHSP_17.6-L_JF7027_    CTCACTCGATATGTGGGATCCCTTCAAGGATTTTCATGTTCCCACTTCCTCTGTTT
GmHSP_17.6-L_JF7056     CTCACTCGATATGTGGGATCCCTTCAAGGATTTTCATGTTCCCACTTCTTCTGTTT

SOYHSP176_M11317.1      CTGCTGAAAATTCTGCATTTGTGAACACACGTGTGGATTGGAAGGAGACCCAAGAG
GmHSP_17.6-L_BRS133_    CTGCTGAAAATTCTGCATTTGTGAACACACGTGTGGATTGGAAGGAGACCCAAGAG
GmHSP_17.6-L_PI595099   CTGCTGAAAATTCTGCATTTGTGAACACACGTGTGGATTGGAAGGAGACCCAAGAG
GmHSP_17.6-L_256-S_     CTGCTGAAAATTCTGCATTTGTGAACACACGTGTGGATTGGAAGGAGACCCAAGAG
GmHSP_17.6-L_259-S_     CTGCTGAAAATTCTGCATTTGTGAACACACGTGTGGATTGGAAGGAGACCCAAGAG
GmHSP_17.6-L_266-S_     CTGCTGAAAATTCTGCATTTGTGAACACACGTGTGGATTGGAAGGAGACCCAAGAG
GmHSP_17.6-L_JF7002_    CTGCTGAAAATTCTGCATTTGTGAACACACGTGTGGATTGGAAGGAGACCCAAGAG
GmHSP_17.6-L_JF7027_    CTGCTGAAAATTCTGCATTTGTGAACACACGTGTGGATTGGAAGGAGACCCAAGAG
GmHSP_17.6-L_JF7056     CTGCTGAAAATTCTGCATTTGTGAACACACGTGTGGATTGGAAGGAGACCCAAGAG

SOYHSP176_M11317.1      GCACACGTGCTCAAGGCTGATATTCCAGGGCTGAAGAAAGAGGAAGTGAAGGTTCA
GmHSP_17.6-L_BRS133_    GCACACGTGCTCAAGGCTGATATTCCAGGGCTGAAGAAAGAGGAAGTGAAGGTTCA
GmHSP_17.6-L_PI595099   GCACACGTGCTCAAGGCTGATATTCCAGGGCTGAAGAAAGAGGAAGTGAAGGTTCA
GmHSP_17.6-L_256-S_     GCACACGTGCTCAAGGCTGATATTCCAGGGCTGAAGAAAGAGGAAGTGAAGGTTCA
GmHSP_17.6-L_259-S_     GCACACGTGCTCAAGGCTGATATTCCAGGGCTGAAGAAAGAGGAAGTGAAGGTTCA
GmHSP_17.6-L_266-S_     GCACACGTGCTCAAGGCTGATATTCCAGGGCTGAAGAAAGAGGAAGTGAAGGTTCA
GmHSP_17.6-L_JF7002_    GCACACGTGCTCAAGGCTGATATTCCAGGGCTGAAGAAAGAGGAAGTGAAGGTTCA
GmHSP_17.6-L_JF7027_    GCACACGTGCTCAAGGCTGATATTCCAGGGCTGAAGAAAGAGGAAGTGAAGGTTCA
GmHSP_17.6-L_JF7056     GCACACGTGCTCAAGGCTGATATTCCAGGGCTGAAGAAAGAGGAAGTGAAGGTTCA

SOYHSP176_M11317.1      GATTGAAGATGATAGGGTTCTTCAGATTAGCGGAGAGAGGAACGTTGAGAAGGAAG
GmHSP_17.6-L_BRS133_    GATTGAAGATGATAGGGTTCTTCAGATTAGCGGAGAGAGGAACGTTGAGAAGGAAG
GmHSP_17.6-L_PI595099   GATTGAAGATGATAGGGTTCTTCAGATTAGCGGAGAGAGGAACGTTGAGAAGGAAG
GmHSP_17.6-L_256-S_     GATTGAAGATGATAGGGTTCTTCAGATTAGCGGAGAGAGGAACGTTGAGAAGGAAG
GmHSP_17.6-L_259-S_     GATTGAAGATGATAGGGTTCTTCAGATTAGCGGAGAGAGGAACGTTGAGAAGGAAG
GmHSP_17.6-L_266-S_     GATTGAAGATGATAGGGTTCTTCAGATTAGCGGAGAGAGGAACGTTGAGAAGGAAG
GmHSP_17.6-L_JF7002_    GATTGAAGATGATAGGGTTCTTCAGATTAGCGGAGAGAGGAACGTTGAGAAGGAAG
GmHSP_17.6-L_JF7027_    GATTGAAGATGATAGGGTTCTTCAGATTAGCGGAGAGAGGAACGTTGAGAAGGAAG
GmHSP_17.6-L_JF7056     GATTGAAGATGATAGGGTTCTTCAGATTAGCGGAGAGAGGAACGTTGAGAAGGAAG

SOYHSP176_M11317.1      ACAAGAACGACACGTGGCATCGCGTGGACCGTAGCAGTGGAAAGTTCATGAGAAGG
GmHSP_17.6-L_BRS133_    ACAAGAACGACACGTGGCATCGCGTGGAGCGTAGCAGTGGAAAGTTCATGAGAAGG
GmHSP_17.6-L_PI595099   ACAAGAACGACACGTGGCATCGCGTGGAGCGTAGCAGTGGAAAGTTCATGAGAAGG
GmHSP_17.6-L_256-S_     ACAAGAACGACACGTGGCATCGCGTGGAGCGTAGCAGTGGAAAGTTCATGAGAAGG
GmHSP_17.6-L_259-S_     ACAAGAACGACACGTGGCATCGCGTGGAGCGTAGCAGTGGAAAGTTCATGAGAAGG
GmHSP_17.6-L_266-S_     ACAAGAACGACACGTGGCATCGCGTGGAGCGTAGCAGTGGAAAGTTCATGAGAAGG
GmHSP_17.6-L_JF7002_    ACAAGAACGACACGTGGCATCGCGTGGAGCGTAGCAGTGGAAAGTTCATGAGAAGG
GmHSP_17.6-L_JF7027_    ACAAGAACGACACGTGGCATCGCGTGGAGCGTAGCAGTGGAAAGTTCATGAGAAGG
GmHSP_17.6-L_JF7056     ACAAGAACGACACGTGGCATCGCGTGGAGCGTAGCAGTGGAAAGTTCATGAGAAGG
```

(CONTINUATION) FIGURE 8

```
SOYHSP176_M11317.1     TTCAGATTGCCAGAGAATGCAAAAGTGGAGCAAGTAAAGGCTTGTATGGAAAATGG
GmHSP_17.6-L_BRS133_   TTCAGATTGCCAGAGAATGCAAAAGTGGAGCAAGTAAAGGCTTGTATGGAAAATGG
GmHSP_17.6-L_PI595099  TTCAGATTGCCAGAGAATGCAAAAGTGGAGCAAGTAAAGGCTTGTATGGAAAATGG
GmHSP_17.6-L_256-S_    TTCAGATTGCCAGAGAATGCAAAAGTGGAGCAAGTAAAGGCTTGTATGGAAAATGG
GmHSP_17.6-L_259-S_    TTCAGATTGCCAGAGAATGCAAAAGTGGAGCAAGTAAAGGCTTGTATGGAAAATGG
GmHSP_17.6-L_266-S_    TTCAGATTGCCAGAGAATGCAAAAGTGGAGCAAGTAAAGGCTTGTATGGAAAATGG
GmHSP_17.6-L_JF7002_   TTCAGATTGCCAGAGAATGCAAAAGTGGAGCAAGTAAAGGCTTGTATGGAAAATGG
GmHSP_17.6-L_JF7027_   TTCAGATTGCCAGAGAATGCAAAAGTGGAGCAAGTAAAGGCTTGTATGGAAAATGG
GmHSP_17.6-L_JF7056_   TTCAGATTGCCAGAGAATGCAAAAGTGGAGCAAGTAAAGGCTTGTATGGAAAATGG

SOYHSP176_M11317.1     GGTTCTCACTGTTACTATTCCAAAGGAAGAGGTTAAGAAGTCTGATGTTAAGCCTA
GmHSP_17.6-L_BRS133_   GGTTCTCACTGTTACTATTCCAAAGGAAGAGGTTAAGAAGTCTGATGTTAAGCCTA
GmHSP_17.6-L_PI595099  GGTTCTCACTGTTACTATTCCAAAGGAAGAGGTTAAGAAGTCTGATGTTAAGCCTA
GmHSP_17.6-L_256-S_    GGTTCTCACTGTTACTATTCCAAAGGAAGAGGTTAAGAAGTCTGATGTTAAGCCTA
GmHSP_17.6-L_259-S_    GGTTCTCACTGTTACTATTCCAAAGGAAGAGGTTAAGAAGTCTGATGTTAAGCCTA
GmHSP_17.6-L_266-S_    GGTTCTCACTGTTACTATTCCAAAGGAAGAGGTTAAGAAGTCTGATGTTAAGCCTA
GmHSP_17.6-L_JF7002_   GGTTCTCACTGTTACTATTCCAAAGGAAGAGGTTAAGAAGTCTGATGTTAAGCCTA
GmHSP_17.6-L_JF7027_   GGTTCTCACTGTTACTATTCCAAAGGAAGAGGTTAAGAAGTCTGATGTTAAGCCTA
GmHSP_17.6-L_JF7056_   GGTTCTCACTGTTACTATTCCAAAGGAAGAGGTTAAGAAGTCTGATGTTAAGCCTA

SOYHSP176_M11317.1     TAGAAATCTCTGGTTAA
GmHSP_17.6-L_BRS133_   TAGAAATCTCTGGTTAA
GmHSP_17.6-L_PI595099  TAGAAATCTCTGGTTAA
GmHSP_17.6-L_256-S_    TAGAAATCTCTGGTTAA
GmHSP_17.6-L_259-S_    TAGAAATCTCTGGTTAA
GmHSP_17.6-L_266-S_    TAGAAATCTCTGGTTAA
GmHSP_17.6-L_JF7002_   TAGAAATCTCTGGTTAA
GmHSP_17.6-L_JF7027_   TAGAAATCTCTGGTTAA
GmHSP_17.6-L_JF7056_   TAGAAATCTCTGGTTAA
```

FIGURE 9

```
                          10        20        30        40        50
SOYHSP176-M11317_1    MSLIPSI  PRSNV DP SLDM DP KD HVPTSSVS ENS  VNTRVD
Gmhsp-17_6-L-BRS133   MSLIPSI  PRSNV DP SLDM DP KD HVPTSSVS ENS  VNTRVD
Gmhsp-17_6-L-PI595099 MSLIPSI  PRSNV DP SLDM DP KD HVPTSSVS ENS  VNTRVD
Gmhsp-17_6-L-256-S    MSLIPSI  PRSNV DP SLDM DP KD HVPTSSVS ENS  VNTRVD
Gmhsp-17_6-L-259-S    MSLIPSI  PRSNV DP SLDM DP KD HVPTSSVS ENS  VNTRVD
Gmhsp-17_6-L-266-S    MSLIPSI  PRSNV DP SLDM DP KD HVPTSSVS ENS  VNTRVD
Gmhsp-17_6-L-JF7002   MSLIPSI  PRSNV DP SLDM DP KD HVPTSSVS ENS  VNTRVD
Gmhsp-17_6-L-JF7027   MSLIPSI  PRSNV DP SLDM DP KD HVPTSSVS ENS  VNTRVD
Gmhsp-17_6-L-JF7056-  MSLIPSI  PRSNV DP SLDM DP KD HVPTSSVS ENS  VNTRVD 60        70        80        90       100
SOYHSP176-M11317_1     KETQE HVLK DIP LKKEEVKVQIEDDRVLQIS ERNVEKEDKNDTWH
Gmhsp-17_6-L-BRS133    KETQE HVLK DIP LKKEEVKVQIEDDRVLQIS ERNVEKEDKNDTWH
Gmhsp-17_6-L-PI595099  KETQE HVLK DIP LKKEEVKVQIEDDRVLQIS ERNVEKEDKNDTWH
Gmhsp-17_6-L-256-S     KETQE HVLK DIP LKKEEVKVQIEDDRVLQIS ERNVEKEDKNDTWH
Gmhsp-17_6-L-259-S     KETQE HVLK DIP LKKEEVKVQIEDDRVLQIS ERNVEKEDKNDTWH
Gmhsp-17_6-L-266-S     KETQE HVLK DIP LKKEEVKVQIEDDRVLQIS ERNVEKEDKNDTWH
Gmhsp-17_6-L-JF7002    KETQE HVLK DIP LKKEEVKVQIEDDRVLQIS ERNVEKEDKNDTWH
Gmhsp-17_6-L-JF7027    KETQE HVLK DIP LKKEEVKVQIEDDRVLQIS ERNVEKEDKNDTWH
Gmhsp-17_6-L-JF7056    KETQE HVLK DIP LKKEEVKVQIEDDRVLQIS ERNVEKEDKNDTWH 110       120       130       140       150
SOYHSP176-M11317_1    RVDRS K MRR RLPEN KVEQVK CMEN VLTVTIPKEEVRKSDVKPIEISG-
Gmhsp-17_6-L-BRS133   RVERS K MRR RLPEN KVEQVK CMEN VLTVTIPKEEVRKSDVKPIEISG-
Gmhsp-17_6-L-PI595099 RVERS K MRR RLPEN KVEQVK CMEN VLTVTIPKEEVRKSDVKPIEISG-
Gmhsp-17_6-L-256-S    RVERS K MRR RLPEN KVEQVK CMEN VLTVTIPKEEVRKSDVKPIEISG-
Gmhsp-17_6-L-259-S    RVERS K MRR RLPEN KVEQVK CMEN VLTVTIPKEEVRKSDVKPIEISG-
Gmhsp-17_6-L-266-S    RVERS K MRR RLPEN KVEQVK CMEN VLTVTIPKEEVRKSDVKPIEISG-
Gmhsp-17_6-L-JF7002   RVERS GK MRR RLPEN KVEQVK CMEN VLTVTIPKEEVRKSDVKPIEISG-
Gmhsp-17_6-L-JF7027   RVERS K MRR RLPEN KVEQVK CMEN VLTVTIPKEEVRKSDVKPIEISG-
Gmhsp-17_6-L-JF7056   RVERS K MRR RLPEN KVEQVK CMEN VLTVTIPKEEVRKSDVKPIEISG-
```

FIGURE 17

| Heat Stress | | | | | |
|---|---|---|---|---|---|
| CH - 25°C/2h | CH - 35°C/2h | CH - 45°C/2h | CH - 25°C/4h | CH - 45°C/4h | CH - 35°C/4h |
| CP - 25°C/2h | CP - 35°C/2h | CP - 45°C/2h | CP - 25°C/4h | CP - 45°C/4h | CP - 35°C/4h |
| S - 25°C/2h | S - 35°C/2h | S - 45°C/2h | S - 25°C/4h | S - 45°C/4h | S - 35°C/4h |
| R - 25°C/2h | R - 35°C/2h | R - 45°C/2h | R - 25°C/4h | R - 45°C/4h | R - 35°C/4h |

| CH - 25°C/24h | CH - 35°C/24h | CH - 45°C/24h |
|---|---|---|
| CP - 25°C/24h | CP - 35°C/24h | CP - 45°C/24h |
| S - 25°C/24h | S - 35°C/24h | S - 45°C/24h |
| R - 25°C/24h | R - 35°C/24h | R - 45°C/24h |

| Cold Stress | | | | | |
|---|---|---|---|---|---|
| CH - 4°C/2h | CH - 15°C/2h | CH - 4°C/4h | CH - 15°C/4h | CH - 4°C/24h | CH - 15°C/24h |
| CP - 4°C/2h | CP - 15°C/2h | CP - 4°C/4h | CP - 15°C/4h | CP - 4°C/24h | CP - 15°C/24h |
| S - 4°C/2h | S - 15°C/2h | S - 4°C/4h | S - 15°C/4h | S - 4°C/24h | S - 15°C/24h |
| R - 4°C/2h | R - 15°C/2h | R - 4°C/4h | R - 15°C/4h | R - 4°C/24h | R - 15°C/24h |

| Salt Stress - NaCl | | Control | Drought Stress | | |
|---|---|---|---|---|---|
| CH - 200mM | CH - 400mM | CH - H₂O | CH - 37°C/2h | CH - 37°C/4h | CH - 37°C/6h |
| CP - 200mM | CP - 400mM | CP - H₂O | CP - 37°C/2h | CP - 37°C/4h | CP - 37°C/6h |
| S - 200mM | S - 400mM | S - H₂O | S - 37°C/2h | S - 37°C/4h | S - 37°C/6h |
| R - 200mM | R - 400mM | R - H₂O | R - 37°C/2h | R - 37°C/4h | R - 37°C/6h |

| Nematode Stress | | | | | |
|---|---|---|---|---|---|
| Control | Juveniles | Control | Juveniles | Control | Juveniles |
| CH - S/J | CH - J/24h | CH - S/J/48h | CH - J/48h | CH - S/J/72h | CH - J/72h |
| CP - S/J | CP - J/24h | CP - S/J/48h | CP - J/48h | CP - S/J/72h | CP - J/72h |
| S - S/J | S - J/24h | S - S/J/48h | S - J/48h | S - S/J/72h | S - J/72h |
| R - S/J | R - J/24h | R - S/J/48h | R - J/48h | R - S/J/72h | R - J/72h |

USE OF AT(N) INSERTIONS IN PROMOTER ELEMENTS FOR CONTROLLING THE EXPRESSION LEVELS OF CODING SEQUENCES IN PLANTS

FIELD OF THE INVENTION

The present invention is related to the use of $AT_{(n)}$ insertions in specific points in the promoter region sequence towards controlling the expression levels of coding sequences in plants, which can be artificially up-regulated (upstream) or down-regulated (downstream), within certain limits.

BACKGROUND OF THE INVENTION

The promoter region of a gene consists in a DNA sequence with generally 1 to 100 and 200 base pairs, upstream from the gene transcription start site and typically contains and/or is adjacent to one or more transcription factor binding sites. All the genes have transcription regulating upstream (above) and downstream (below) the transcription start site. The transcription factors recognize and bind to these regulating sequences, controlling the synthesis of the transcribed messenger RNA. These sequences include promoters, enhancers and regulating sequences. The promoters can be used in gene constructs, manipulated by means of genetic engineering, to overexpress, inhibit or modulate the expression of genes, in constitutive mode or induced by certain circumstances.

Various techniques for overexpressing genes are presently available in the field of Biotechnology, whereof the main technique comprises the construction of expression cassettes containing the constitutive promoter 35S, isolated from the cauliflower mosaic virus (CaMV—Cauliflower Mosaic Virus). There are however some exceptions to the use of this promoter in gene constructs. The use of a small sequence of viral DNA and the insertion thereof into the genome of a plant have proven experimentally the existence of a potential risk of genetic recombination between the genome of the virus that is infecting a plant and that of the transgenic plant, or more precisely, between the messenger RNA transcript. The risk would amount to the creation of a new virus strain, possibly of more virulent type.

The promoter 35S CaMV is considered promiscuous and functions effectively in all plants, as well as in green algae, yeasts *E. coli*. It has a modular structure with parts in common and interchangeable with promoters of other plant and animal viruses. It also has a recombination hotspot, flanked by multiple motives involved in the recombination process, similar to other recombination hotspots, including the borders of the T-DNA vector of *Agrobacterium* sp., frequently used in transgenic plants. This hotspot tends to split and bind to other DNAs and thereby increases the probabilities of horizontal gene transfer and recombination processes. Therefore, the potential risks are mutagenesis and carcinogenesis, due to insertions of the invasive exogenous DNA into the genomes, the reactivation of dormant viroses and the generation of new viroses, which will only be stable if they contribute some selective advantage over the wild type of the virus.

Partial or full transgenic events and/or inhibition of expression of endogenous homologues were observed using the promoter 35S CaMV (Napoli et al (1990) The Plant Cell 2: 279-289; Van der Krol at al (1990) Plant Cell 2 291-299). This inactivation occurs due to complex mechanisms involving methylations and epigenetic alterations (Renckens et al (1992) Mol. Gen. Genet. 233: 53-64; Neuhuber et al (1994) Mol. Gen. Genet. 244: 230-241; Meyer & Heidmann (1994) Mol. Gen. Genet. 243: 390-399; Thierry & Vaucheret (1996) Plant Mol. Biol. 32: 1075-1083. Although the actual mechanism that indicates certain sequences to the methyltransferases or other enzymes responsible for the epigenetic alterations remains unknown, there are hypotheses to suggest the involvement of interactions of dependent homologues between DNA-DNA, DNA-RNA and RNA-RNA (Grierson et al. (1991) Trends in Biotechnology 9: 122-123); Matzke & Matzke (1995) Plant Physiology 107: 679-685.

In the literature there is data evidencing that CaMV genes incorporated into canola chromosomes recombined with the genome of infecting viruses and produced new and more virulent viroses.

These recombinations between CaMV viroses involve promoter regions (Vaden & Melcher (1992) Virology 177: 717), and may take place between DNA and DNA or between RNA and RNA and often give rise to infections that are more severe than the parental counterparts (Mol. Plant-Microbe Interactions 5: 48, 1992).

The use of the promoter 35S CaMV further usually results in the expression of products of the exogenous gene at rates lower than 1% of the total protein. Some improvements in this promoter, such as the duplication of some sequences and the addition of enhancers increased the expression thereof, but for some applications the expression levels of the exogenous gene products need to be further increased.

In general, in experiments having been conducted using the constitutive promoter 35S CaMV to obtain genetically modified plants for the characteristic of tolerance to biotic and abiotic stresses, it is reported that although the tolerance is increased in some cases, one of the undesired effects derived from the use of this promoter is the reduction of size of the plants, whose growth and development are normally affected, resulting in small plants irrespective of the plant species that was transformed (Kasuga et al. (1999) Nature America Inc. 287-291).

Therefore, although some negative effects such as delay in plant growth may take place, strategies like the use of stress-induced promoters to control gene expression may prevent or mitigate such effects.

In another work, Gelvin et al. (Plant Molecular Biology Manual. Norwell, Mass.: Kluwer Acedemic Publishers, 1995) analyzed the expression of GUS directed by some promoters constructed with various combinations of regulating sequences of two genes of the bacterium *Agrobacterium tumefaciens*: opine synthase (ocs) and mannopine synthase (mas). And among the various combinations, a hybrid promoter formed by the triple repetition of the ocs gene activating sequence fused with mas activating elements and mas promoter region, named "(Aocs)3AmasPmas", exhibited in transformed tobacco cells expression levels of the GUS marker gene that were 10 times larger when compared to cells containing the promoter CaMV 35S. This new promoter did not affect the transformation efficiency, however the high level of expression of the marker gene facilitated the identification of larger proportions of transformed cells. The expression levels were high in leaves, roots and various cell types. This promoter was also very active in manioc and pea plants, two crops difficult to transform using *Agrobacterium* sp. This group, further using this promoter "(Aocs)3AmasPmas", described the success in studying the fast transcription of genes introduced (after 18 hours) into tobacco and corn plants, differently from the expression controlled by the promoter CaMV 35S, which activity is weak and does not allow any detection of genetic expression within this time span.

There is a further option of using stress-induced promoters for overexpression of genes in gene constructs, and in this regard the promoter rd29, isolated from *Arabdopsis thaliana*, is the most used in the search for plants with better tolerance to abiotic stresses. As a rule, these genetic constructs are always fused to genes of the family DREB (*Dehydration Responsive Element Binding*) that control the expression of genes in response to environmental stresses such as drought, salinity and low and high temperatures. In some works that used different plant species there were reported as the result of genetic transformation with induced stress promoters, plants that were more tolerant to abiotic stresses (Oono et al., (2003) The Plant Journal, 34: 868-887; Kasuga et al. (2004) Plant Cell Physiol 45(3):346-350.

Fuganti et al. (2004) used soybean genotypes resistant and susceptible to cyst nematode. The document contains the initial data on molecular markers that would be used in assisted selection of soybean genotypes resistant to the cyst nematode. However, there was not detected any type of molecular difference between the individuals having been tested, regarding the level of DNA sequence or expression of mRNA encoded by the gene.

Fuganti (Master's Thesis, State University of Londrina [Universidade Estadual de Londrina], 2004) presented the selection of resistant strains, using molecular markers associated with genes of resistance and of molecular characterization of genomic regions comprising those genes of interest. In this work there is not disclosed qualitative or quantitative data to indicate a possible correlation between the size of the AT(n) insertions in the gene promoter region and the resulting level of expression of its mRNA or protein. The present invention proposes the ability to control and/or to up-regulate or down-regulate the expression level of any provided that there are inserted into the promoter regions certain numbers of $AT_{(n)}$ insertions. Such proposal is neither presented nor tested in this work.

Fuganti (PhD Thesis, State University of Maringá [Universidade Estadual de Maringá], 2007) presented quantitative and qualitative data that indicates a possible correlation between the different sizes of the $AT_{(n)}$ insertion within the promoter region of the gene Gmhsp17.6-L and the level of expression thereof in response to various abiotic and biotic stresses (cold, heat, drought, salinity, infection by nematode juveniles). However, the possibility of up-regulating or down-regulating the expression level of any gene, which coding region may be fused to the promoter regions containing different $AT_{(n)}$ sizes, in the absence and/or presence of biotic and abiotic stresses was neither presented nor discussed.

Patent document No. US2005059623 provides methods of use of local heat, by means of controlled application of ultrasound, to control the expression of a therapeutic gene, fused to the heat shock protein (HSP) promoter, expressed in selected cells. The proposed invention is aimed at controlling and up-regulating or down-regulating the expression level of any gene fused to the promoter regions of a heat shock protein that has in its gene sequence different sizes of $AT_{(n)}$ insertions expressed in all the transformed cells. Biotic or abiotic stresses may be applied to the entire plant. There is not disclosed any indication of the role of the AT insertions in the control of the gene expression, or of the possibility of use thereof as a tool to regulate the expression of any gene, provided that the same are inserted into the promoter region thereof.

Patent document US2003190706 relates to an exogenous gene fused to a DNA sequence that exhibits promoter activity, which would promote an increase in the total amount of the gene product (proteins). This region with promoter activity was produced from mutagenic alterations including substitutions and deletions of nitrogenized bases. The present invention requires the use of a complete gene promoter, containing all the gene elements required to induce the synthesis of mRNAs. It is clear in the present invention that the control of the gene expression would result in levels differentiated according to the size of the $AT_{(n)}$ insertions, rather than random mutations in the promoter region of the gene.

Patent document EP1930423 discloses a promoter region of a heat shock protein, split into different final sizes, that is used in a system for the production of heterologous protein, whose expression levels are not controlled by means of other conventional promoters. In order to activate the expression there are used specific stresses, either abiotic or chemical. The present invention uses a previously existing variation in the genotypes studied, smaller than the 1000 bp fragment used in document EP1930423, and detected in the promoter region of the gene Gmhsp17.6-L. This variation is provided by the different numbers of $AT_{(n)}$ insertions in specific regions of the promoter, resulting in size variations between 312 bp ($AT_9$) and 358 bp ($AT_{33}$) depending on the $AT_{(n)}$ insertion.

U.S. Pat. No. 5,929,302 uses a temporal and tissue-specific promoter, which regulates the gene expression at the time of maturity, in tissues such as leaves and receptacles. The promoter was isolated from the dru gene itself, or from its homologue, in raspberries, to express chimeric genes. There is suggested the combination of this promoter with specific genes such as genes that regulate the change of color and flavor, genes of enzymes or catabolic products that modify plant cell processes, genes whose products affect the synthesis of ethylene, alternative fungal control genes and sucrose accumulating genes. The present invention proposes alterations in the promoter region of any gene, in order to alter the expression thereof in all cells and throughout the entire life cycle of the plant. The variation of the expression level of the gene product would be correlated with the different numbers of $AT_{(n)}$ insertions into the promoter, and consequently with promoters of different sizes. The invention proposes to control the expression of any gene containing these alterations.

Therefore, the present invention is innovative, as it differs from all presently existing methodologies available in the scientific literature to overexpress genes. To do so, the invention uses the insertion of an AT sequence with a greater and smaller number of repetitions, enabling the modulation of the levels of gene expression, increasing or reducing the same.

SUMMARY OF THE INVENTION

The present invention refers to the use of $AT_{(n)}$ insertions in promoter elements for controlling the expression levels of coding sequences in plants. The invention also refers to gene expression cassettes containing promoter regions of the gene with different numbers of AT insertions fused to the GUS protein, to transform soybean embryos.

The present invention provides a method for regulating expression levels of coding sequences in plants comprising:
(i) stably transforming a plant cell with an expression cassette carrying $AT_{(n)}$ insertions within the promoter element operably linked to gene of interest.

(ii) culturing the stably transformed plant cell under plant cell growing conditions;

(iii) regenerating a transgenic plant having stably incorporated into its genome the cassette of (i);

Wherein said transgenic plant shows different levels of gene expression when compared to control plants.

The invention further provides expression cassettes comprising two promoter regions having different numbers of AT-insertions linked to the promoter region of Gmhsp17.6-L gene.

Another embodiment of the invention is process provided for obtaining genetically modified plants comprising $AT_{(n)}$-insertions, wherein said method comprises:

(i) stably transforming a plant cell with an expression cassette carrying $AT_{(n)}$ insertions within the promoter element operably linked to gene of interest;

(ii) culturing the stably transformed plant cell under plant cell growing conditions;

(iii) regenerating a stably genetically modified plant.

The results suggest that the expression level of a certain gene can be artificially up-regulated (upstream) or down-regulated (downstream), within certain limits, by inserting, via genetic engineering tools, $AT_{(n)}$ repetition bases inside the promoter region.

DESCRIPTION OF THE DRAWINGS

The patent or application file contains at least one drawing executed in color. Copies of this patent or patent application publication with color drawings will be provided by the office upon request and payment of the necessary fee.

FIG. 2 shows the sequence of the gene Gmhsp17.6-L, available from the GenBank (access number: M11317 (residues 1-900 of SEQ ID NO: 18)). The underlines, the primers pSoyHspPstI_F and pSoyHspBamHI_R define the amplified fragment of the promoter region. In dotted box, the $AT_{(n)}$ insertion and, in gray box, start (ATG) and stop (TAA) codon of the coding region.

FIG. 3 shows the sequence of the gene Gmhsp17.6-L (access number at the GenBank: M11317 (residues 1-900 of SEQ ID NO: 18)). In gray box, start (ATG) and stop (TAA) codon defining the coding region, in dotted box highlight the $AT_{(n)}$ insertion in the promoter region and, in underline, the primers pSoyHsp_F and SoyHSP Cl_R designed for complete sequencing of the gene.

FIG. 6 shows the alignment of the sequences of the promoter region of the gene Gmhsp17.6-L; determined from GenBank Accession No. M11317 (residues 1-323 of SEQ ID NO: 18), and generated by the amplification of the resistant parent individuals PI595099 (SEQ ID NO: 20), susceptible parental BRS133 (SEQ ID NO: 19), individuals of the susceptible population 256-S(SEQ ID NO: 21), 259-5 (SEQ ID NO: 22) and 266-S (SEQ ID NO: 21) and individuals of the resistant population JF7002 (SEQ ID NO: 23), JF7027 (SEQ ID NO: 20) and JF7056 (SEQ ID NO: 24), with the set of primers pSoyHSPPstI_F and pSoyHSPBamHI_R which define the promoter region. The primers were designed based on complete sequence of the gene Gmhsp17.6-L (access number at GenBank: M11317). In dotted box is the $AT_{(n)}$ insertion. In box, probable TATA-box. In black box with white letters is one of the heat shock elements (HSEs) of consensus sequence 5'AGAAnnTTCT3' (SEQ ID NO: 1). In gray box with white letters, another consensus sequence 5'cTTCtaGAAgcTTCtaGAAg3' (SEQ ID NO: 2) of another HSEs, with core 5'CTnGAAnnTTCnAG3' (SEQ ID NO: 3).

FIG. 7 shows the alignment of the gene sequence existing between the end of the promoter region of the gene Gmhsp17.6-L and the start of the coding region, materials under study parental, susceptible (BRS133 (SEQ ID NO: 28)) and resistant (PI595099 (SEQ ID NO: 25)), and individuals of the susceptible population, 256-S(SEQ ID NO: 28), 259-5 (SEQ ID NO: 25) and 266-S(SEQ ID NO: 28), and of the resistant population, JF7002 (SEQ ID NO: 25), JF7027 (SEQ ID NO: 25) and JF7056 (SEQ ID NO: 25), compared with the sequence of the gene available at the GenBank (access number: M11317 (SEQ ID NO: 25)). Nucleotides in gray box highlight the codon ATG of the transcription start site of the coding region.

FIG. 8 shows the alignment of the coding sequence of the gene Gmhsp17.6-L originating from all materials under study, susceptible parentals BRS133 (SEQ ID NO: 26) and resistant PI595099 (SEQ ID NO: 26), and individuals of the susceptible population, 256-S(SEQ ID NO: 26), 259-5 (SEQ ID NO: 26) and 266-S (SEQ ID NO: 26), and of the resistant population, JF7002 (SEQ ID NO: 26), JF7027 (SEQ ID NO: 26) and JF7056 (SEQ ID NO: 26), compared with the sequence of the gene available at the GenBank (access number: M11317 (SEQ ID NO: 26)). Nucleotides in gray box highlight the ATG start codon and TAA heat transcription codon, defining the coding region.

FIG. 9 shows the alignment of the sequence of amino acids encoded by the coding region of the gene Gmhsp17.6-L originating from all materials under study, susceptible parentals BRS133 (SEQ ID NO: 27) and resistant PI595099 (SEQ ID NO: E), and individuals of the susceptible population, 256-S(SEQ ID NO: 27), 259-5 (SEQ ID NO: 27) and 266-S(SEQ ID NO: 27), and of the resistant population, JF7002 (SEQ ID NO: 27), JF7027 (SEQ ID NO: 27) and JF7056 (SEQ ID NO: 27), compared with the sequence of the gene available at the GenBank (access number: M11317 (SEQ ID NO: 27).

FIG. 17 shows a schematic model illustrating the structure of the test plaque of the abiotic and biotic stresses, to which soybean embryos of cultivars susceptible to cyst nematode, BRS133 and Pintado (speckled), transformed with different expression cassettes, were submitted. ON—negative control, embryos not transformed; CP—positive control, embryos transformed with plasmid pAG1; S—embryos transformed with expression cassette constructed with the promoter region originating from the susceptible parental, pAG1/promotorGmHSP_BRS133; R embryos transformed with expression cassette constructed with the promoter region originating from the individual of the resistant population, pAG1/promotorGmHSP_JF7027.

DETAILED DESCRIPTION OF THE INVENTION

Figure 1:
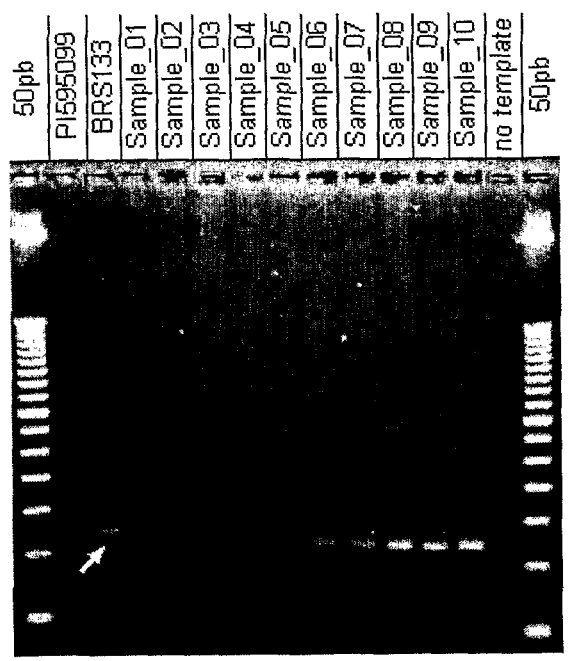
FIG. 1 shows the agarose gel with the amplification of the microsatellite marker SOYHSP 176, in the resistant parental sample, PI595099, in the susceptible parental BRS 133, and in individuals of the resistant population (Sample_01 to Sample_05) and susceptible (Sample_06 to Sample_10). The arrow indicates the band generated by the amplification of the marker in the susceptible parentals, which also appears in the susceptible population.

The present invention refers to the use of $AT_{(n)}$ insertions in promoter elements for controlling the expression level of coding sequences in plants. A comparison was made of the expression levels of the heat shock protein (Gmhsp17.6-L), among resistant and susceptible individuals in the population, and it was noted that the largest expression levels per quantitative PCR were present in the individuals containing the largest AT insertions in the promoter region. Gene expression cassettes were constructed containing promoter regions of the gene with different numbers of AT insertions fused to the GUS protein, to transform soybean embryos. The results of the experiments of the present invention suggest that the expression level of a certain gene could be artificially up-regulated (upstream) or down-regulated (downstream), within certain limits, by inserting, via genetic engineering tools, $AT_{(n)}$ repetition bases inside the promoter region. Hence, the technology developed in the present invention permits the control of the expression levels of genes, provided that the $AT_{(n)}$ repetition insertions are inserted in specific points in the sequence of the promoter region.

Based on prior studies seeking to identify molecular markers for use in assisted selection of soybean genotypes resistant to the nematode *Meloidogyne javanica*, the microsatellite marker, SOYHSP 176, of the F bond group, presented high significance for the populations tested, explaining for the character number of cysts in the root, 43% of the phenotypic variation and for note in descriptive scale 70% of the variation. It is important to point out that the fragment amplified by this marker was only present in the susceptible individuals, being absent in the resistant individuals.

This marker was sequenced and after searching for similarities with other sequences of nucleic acids deposited in gene banks, this sequence revealed high homology with the promoter region of a low molecular weight heat shock protein (Gmhsp17.6-L), found in the soybean, and deposited at the GenBank (access number: M11317). Using the complete sequence of this gene available at the GenBank, new pairs of primers were designed, seeking to amplify the fragment in both genotypes.

The strategy was successful and fragments were obtained both in the susceptible individuals as in the resistant individuals. All the resulting fragments were cloned and sequenced, also showing homology with the same promoter region of the gene Gmhsp17.6-L. However, the alignment of the sequences showed that the resistant plants when compared to the susceptible plants, have in the promoter region of the gene, a greater insertion of microsatellite, characterized by $AT_{(n)}$ repetitions. Thus, the fragments originating from the resistant parental PI 595099, presented 15 and 13 AT additional repetitions when compared with the sequence of the gene Gmhsp17.6-L, available at the GenBank. On the other hand, the fragment originating from the susceptible parental BRS 133, has six AT repetitions less than the sequence available at the GenBank. These results were repeated for the resistant and susceptible individuals of the population resulting from this cross-breading which were also sequenced.

The alignment also indicated that all the fragments amplified had the sequence complementary to the primers of the microsatellite marker SOYHSP 176. Having established this, the question then arose: why did the amplification not occur in initially resistant plants, even though the annealing region of the microsatellite primers probably existed? One possibility would be the greater number of AT repetitions in the resistant individuals, provided the formation of some kind of tertiary structure, such as a hairpin, resulting in the difficulty of the primers to anneal during the process of amplifying the DNA polymerase and, consequently, inhibiting the formation of an amplicon in these plants.

It was believed that the insertion of a microsatellite inside the promoter region of this gene would deactivate it in the susceptible plants, since the marker SOYHSP 176 only amplified in these individuals. However, studies revealed that all the samples presented the insertion of a microsatellite, perhaps being the number of AT repetitions inside the promoter region that may be interfering in the soybean's response to the nematode. The presence of a greater or lesser insertion of repeated sequences inside the promoter region of the gene may deactivate, activate or even alter the expression levels of the protein controlled by this promoter.

According to literature, one of the main functions of these AT-elements repeated in the control of the gene expression of the heat shock proteins, is to facilitate the access of the RNA polymerase to the transcription start site, and also to exclude histones in order to facilitate the bond of the heat shock factors (HSFs), responsible for inducing the transcription. The heat shock proteins, according to literature, act in the cell as molecular chaperones, establishing nascent polypetide chains and assisting in their correct folding, reestablishing proteins and/or denatured membranes, and also performing an important role in the signal transduction.

Therefore, to test the hypothesis that the length of the insertion into the promoter region of the gene Gmhsp17.6-L is altering the expression levels of the protein Gmhsp17.6-L in resistant and susceptible individuals infected by *M. javanica*, the Ribonuclease Protection Assay was used. The results showed that all individuals, whether resistant or susceptible, and regardless of the treatment, inoculated or not with the nematode, express the protein. By virtue of the biological function of the AT sequences in gene regulation and the difference existing between the individuals regarding the number of repetitions inside the promoter, it was believed that the ribonuclease protection assay would reveal a difference of expression of the gene Gmhsp17.6-L in the different individuals, yet the results show that theoretically there is no difference in the expression of this gene in response to infection by the nematode, at least not at a level detectable by the technique used.

In the attempt to confirm these results, a new study was devised using a more precise and accurate technique to quantify the gene expression level, the PCR in real time (RT-PCR). Parentals, BRS 133 (susceptible) and PI595099 (resistant) and also three individuals of the susceptible population (256-S, 259-S and 266-S) and resistant (JF7002, JF7027 and JF7056) originating from this cross-breading, were inoculated with the nematode. Roots in the treatments inoculated and non-inoculated with *Meloidogyne javanica*, were collected for extraction of RNA total cDNA synthesis which was subsequently used in the RT-PCR reactions for relative quantification.

The results showed that all resistant and parental individuals, PI595099, and of the population, JF7002, JF7027 and JF7056, present a higher expression of the gene Gmhsp17.6-L in the inoculated treatment with the cyst nematode, *Meloidogyne javanica*. These individuals of the population are the same that, in sequencing, presented higher $AT_{(n)}$ insertion inside the promoter region of the gene. Our hypothesis is that, when being infected by the nematode, the plant produces some factor that interacts with the AT-rich region of the promoter of the gene Gmhsp17.6-L of the resistant plant, activating the transcription thereof which would have the function of a chaperone in the cell. In plants sensitive to the interaction of the factor such as the AT region, it would not occur in such an intense way, meaning that the expression levels of the protein Gmhsp17.6-L would be lower in the plants sensitive to the nematode.

Through the technology of the present invention it will be possible to regulate the expression levels of different genes, containing AT insertions of different sizes in specific points of the promoter region. It will also be possible to develop GM plants overexpressing or underexpressing the genes, in proportion to the size of the AT insertion, present in the promoter region.

EXAMPLES

Biological Material

The constructs were developed using soybean genotypes, parental PI595099 and BRS133, resistant and susceptible, respectively, to the gall nematode, *M. javanica*. From this cross, in the $F_4$ generation, the individuals 256-S, 259-S and 266-S, from the susceptible population and the individuals JF7002, JF7027 and JF7056 from the resistant population, were selected and used in the study.

The cultivar Pintado, susceptible to the nematode was also used in the transformation step, through particle bombardment, of soybean embryos using expression cassette constructed from different samples and containing different $AT_{(n)}$ insertions in the promoter region of the gene Gmhsp17.6-L (GenBank accession number: M11317).

Example 1: Isolation and Characterization of the Promoter and the Complete Gene

Using the complete sequence of the gene Gmhsp17.6-L, obtained from the initial sequencing of the amplified fragment of susceptible materials using microsatellite marker Soyhsp 176 primers, new primer sets were designed in order to obtain bands in all genotypes under analysis, given that, initially, only susceptible genotypes amplified the microsatellite marker SOYHSP 176 (FIG. 1).

The primers (pSoyHsp_AleI F 5'CAC CGC GGT G GAA TTC TGA AAT TGG GTC TTT TTG3' (SEQ ID NO: 4); pSoyHsp_NcoL_R 5'CCA TGG AAT GGG GAC ACT CGA GGT ATT3' (SEQ ID NO: 5)) were synthesized in the beginning of the promoter region of the gene Gmhsp17.6-L, adding restriction sites for future cloning. FIG. 2 indicates the primers annealing sites in the sequence of the gene Gmhsp1 7.6-L, available at the GenBank.

More new primer sets (pSoyHSP_PstI_F 5'GGG CTG CAG GAA TTC TGA AAT TGG GTC TTT TTG3' (SEQ ID NO: 6); SoyHSPCL_R 5'CCC CCC GGG TTA ACC AGA GAT TTC TAT AGC CT3' (SEQ ID NO: 7) were designed, in order to amplify the whole gene, from the beginning of the promoter to the stop codon in the coding region, and subsequently, verify the existence of other differences in the gene sequence, besides the $AT_{(n)}$ insertions of the promoter region between the genotypes susceptible and resistant to the gall nematode *M. javanica*. FIG. 3 indicates the primers annealing site in the sequence of the gene Gmhsp1 7.6-L, available at the GenBank, designed to amplify and to sequence the complete gene.

The genomic DNA from seeds was extracted from all the analyzed samples. From each analyzed sample, approximately 50 mg of seeds, sliced in thin sections using a razor blade, were collected in a 1.5 mL microtube and 300 μL of extraction buffer was added. The material was grinded and an extra 700 μL of extraction buffer was added. The extraction buffer was prepared according to the protocol presented in the table below:

TABLE 1

Reagents used in the preparation of
the genomic DNA extraction buffer

| Reagents | Stock conc. | Final conc. | For 10 mL |
|---|---|---|---|
| Tris-HCl pH 7.5 | 1 mol/L | 200 mM | 2 mL |
| NaCl | 5 mol/L | 288 mM | 575 µL |
| EDTA | 500 mM | 25 mM | 500 µL |
| SDS | 10% | 0.5% | 500 µL |
| $H_2O$ | — | — | 6.5 mL |

The solution was homogenized, using a vortex, for 30 s to 1 min and centrifuged for 4 min, at 16.000×g, at room temperature. The supernatant was transferred to a new 1.5 mL tube, submitted to a new centrifugation step at the same previous conditions and, once again, transferred to a new 1.5 mL tube.

In order to eliminate proteins, 0.1 mg of Proteinase K and 0.01 mM of $CaCl_2$ was added to the samples and those were incubated in water bath at 37° C. for 90 min. 900 µL of cold isopropanol was added and, after incubation for 2 min, a centrifugation for 7 min 16.000×g was conducted. The supernatant was discarded and the pellet was dried for 90 min. The pellet was ressuspended in 300 µL of TE buffer (Tris-HCl 1M pH 8.0, EDTA 0.5 M pH 8.0) containing 40 µg/µL of RNase A and the samples were incubated once again in water bath at 37° C. for 90 min in order to eliminate the RNA. Following, a new precipitation step were conducted and, finally, the DNA pellet was ressuspended in 300 µL of TE buffer, quantified using spectrophotometry and its quality and integrity was verified in 0.8% agarose gel.

The PCR reactions in order to amplify the promoter region and the complete gene sequence, from all resistant and susceptible samples, were conducted using Perkin Elmer 9600 thermocycler and were constituted of: 30 ng of template DNA, 10× reaction buffer (100 mM of Tris-HCl pH 8.3, 500 mM of KCl and 400 µL of ultra pure water), 1.5 mM of $MgCl_2$, 1.3 mM of dNTP, 1 U of Taq DNA polymerase and 5 µM of each of the F and R primers, using ultra pure water to complete up to the final volume of 10 µL.

The thermocycling program used to amplify the DNA samples was composed of an initial denaturation step at 94° C. for 7 min, followed by 30 cycles of denaturation at 94° C. for 1 min, annealing at 60° C. for 1 min and extension at 72° C. for 2 min. A 7 min at 72° C. cycle was conducted in the end. The products of amplification were separated in 1% agarose gel, prepared using 1×TBE buffer (108 g Tris base, 55 g boric acid, 40 mL EDTA 0.5 M pH 8.0 and distilled water to complete the final volume of 1 L) and stained in ethidium bromide (10 mg/mL). Images were obtained using the Kodak Digital DC 290 System.

Figure 4:
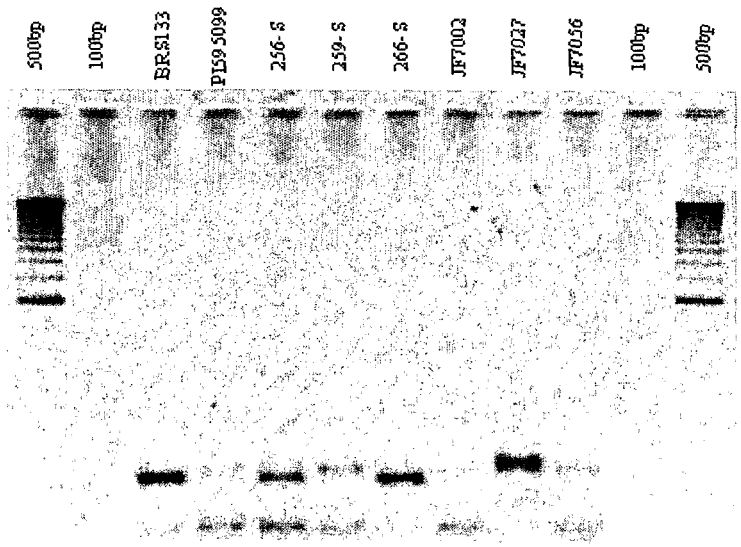
FIG. 4 shows the amplifications of the promoter region of the gene Gmhsp17.6-L, with the primers pSoyHSP_AleI_F and pSoyHSP_NcoI_R, designed based on the complete sequence of the gene available from the GenBank (access number: M11317). Ladder 100 pb and 500 pb.
Figure 5:
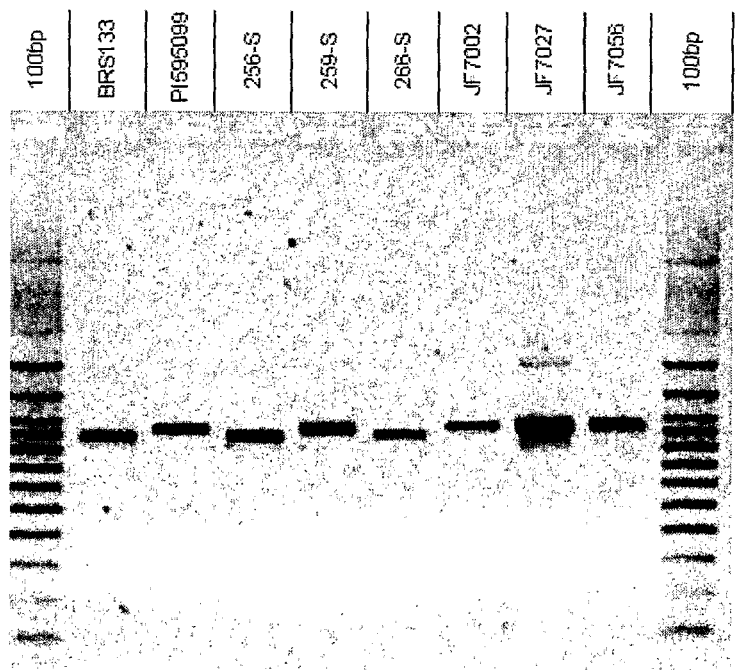
FIG. 5 shows the amplifications of the complete gene Gmhsp17.6-L, with the primers pSoyHSP_PstI_F and pSoyHSP_Cl_R, designed based on complete sequence of the gene available from the GenBank (access number: M11317). Ladder 100 pb and 500 pb.

The amplified fragments (FIGS. 4 and 5) were gel extracted using PureLink™ Quick Gel Extraction (Invitrogen) kit, according to the manufacturer's instructions. The DNA, after being purified, was stored at −20° C. Following, the DNA were quantified and a ligation reaction between the fragment and a plasmidial vector was conducted using the TOPO® TA Cloning kit (Invitrogen). The ligation reaction was composed of 2 µL of ultra pure water; 1 µL of Salt Solution (dilution of 7 µL of Salt Solution: 21 µL of ultra pure water); 1 µL TOPO® vector and 2 µL (~10 ng) of the purified band. The samples were incubated at room temperature for 5 min.

The obtained vector was used for *Escherichia coli* (DH10 B strain) cell transformation, through eletroporation. The eletrocompetent cells were prepared, obtaining isolated colonies through plate streaking from a glycerol stock. Following, a single colony was cultivated overnight in 10 mL of LB media—Luria Bertani (20 g of mixture of tryptone, yeast extract and NaOH for 1 L of distilled water) at 37° C., at 200 rpm (pre-inocule). 5 mL of pre-inocule were added to 500 mL of LB media, at 37° C. with rotation at 300 rpm, until an $OD_{600}$ between 0.5 and 0.7 was reached. After this period, the cells were incubated on ice for 20 min and transferred to ice-pre-chilled 250 mL centrifuge tubes in aseptic manner. A centrifugation step at 4.278×g, for 15 min, at 4° C. was conducted, the supernatant was discarded and the pellet was ressuspended in 500 mL of cold 10% glycerol. A new centrifugation step under the same conditions was conducted, the supernatant was discarded and the pellet was ressuspended in 250 mL of cold 10% glycerol. One more centrifugation step was conducted and the pellet was ressuspended in 20 mL of cold 10% glycerol. The solution was transferred to 50 mL sterile tubes and centrifuged at 3997×g, for 15 min, at 4° C. As a final step, the pellet was ressuspended in 1 mL to 2 mL of 10% of cold glycerol. The eletrocompetent cells were aliquoted in 500 µL microtubes and stored in freezer at −80° C.

The eletroporation was conducted in MicroPulser (Bio-Rad) eletroporator set to 2.5 kV, 25 µF, and pulse controller set at 200 or 400 ohms. 2 µL of the ligation reaction and 100 µL of the eletrocompetent cells were used. The rescue of the cells was obtained by cultivating the bacterial suspension in 1 mL of SOC media (0.5 g of yeast extract, 2 g of tryptone, 10 mM of NaCl, 2.5 mM of KCl, 10 mM of $MgCl_2$, 10 mM of $MgSO_4$, 20 mM Glucose and mL of distilled water), in 15 mL sterile Falcon tube, incubated at 37° C., for 1 h at 200 rpm. After this period, 300 µL of eletroporated cells were plated in solid LB media supplemented with ampicillin (100 µg/30 mL), containing IPTG/X-Gal (50 µl of IPTG—isopropyl-β-thiogalactopyranoside 0.1 M and 10 µL of X-Gal-1-bromo-4-chloro-3-indolyl-β-D-galactoside 50 mg/mL per plate). The plates were incubated at 37° C. overnight for colony growth. The selection of the recombinant clones was conducted using the lac Z system, which recombinant colonies presented white color and non-recombinant colonies, blue color due to the resulting product of the reaction between the lac Z gene product and the substrate (X-Gal).

Following, to confirm the cloning and the size of the fragments, a plasmidial DNA extraction was conducted by inoculation of single white colonies in 96-well microplates, containing 1 mL of CG media—Circle Grow (4 g of commercial mixture for 100 mL of water) and 100 µL/mL of ampicillin (50 µL de ampicillin at 100 mg/mL for 50 mL of CG media). The plate was sealed and the material incubated at 37° C., at 320 rpm, for 22 h.

Before proceeding to the plasmid extraction, a permanent culture of grown bacteria was obtained, containing 75 µL of CG media grown overnight and 75 µL of 50% sterile glycerol in sterile plates. This culture was stored in ultra-freezer at −80° C. to serve as stock.

Proceeding with the miniprep, in order to obtain sedimentation of the cells, the microplate was centrifuged for 6 min, at 1.310×g, at 10° C. The supernatant was discarded and the plate quickly inverted over absorbing paper. Following, 200 µL of GET (20% Glucose, 0.5 M EDTA pH 8.0, 1M Tris-HCl pH 7.4 and water to complete 500 mL) were added to each well, the plate was sealed and agitated using a vortex for 2 min to ressuspend the cells. A new centrifugation for 9 min, at 1.310×g, at 10° C. was conducted, the supernatant was discarded and the plate was inverted over absorbing paper and was dried.

65 µL of GET containing RNase A (10 mg/mL) were added to each well of the microplate. All the material was ressuspended using a vortex and transferred to a plate with "U" bottom. It was added then, to each well, 65 µL of NaOH 0.2N/SDS 1% (0.5 mL NaOH 4M+1 mL SDS 10%+ultra pure water to complete the volume of 10 mL). This solution was prepared just prior the beginning of the step in which it was going to be used. The plate was sealed; the material was mixed by inversion for 5 to 10 times and incubated for 10 min at room temperature. A quick centrifugation for a few seconds was conducted until there was no solution left in the adhesive seal.

To each well, it was added 60 µL of 3 M potassium acetate (KOAc) stored at 4° C., the plate was sealed, the material was mixed by inversion for 10 times and a 10 min incubation was conducted on ice. A centrifugation step of 15 min, at 1.310×g, at 4° C. was performed, and 80 µL of the supernatant was transferred to a Millipore® (MAGV N22) plate, previously fixed on top of a 250 µL "V" bottom polypropylene microplate. The plate was centrifuged for 5 min at 1.310×g, at 4° C., or until the whole volume was transferred to the bottom plate (V bottom). The Millipore® plate was removed and discarded and, to the filtered solution that was transferred to the "V" bottom plate, 80 µL of isopropanol were added.

The "V" bottom plate was sealed using alcohol-resistant adhesive and the material was mixed by inversion. A centrifugation step of 45 min, at 1.310×g, at 4° C., was conducted the supernatant was discarded by inverting the plate and 150 µL of cold 70% ethanol was added to each sample. The plate was centrifuged once again for 5 min, at 1.310×g, at 4° C. and, after the supernatant was discarded, the plate was inverted over absorbing paper and briefly spun down at 82×g, at 4° C. The plate was dried at room temperature covered by paper towel for 60 min and, finally, the DNA was ressuspended in 30 µL of ultra pure water. The plate was sealed and incubated at room temperature overnight for complete elution of plasmidial DNA. After this period, the plate containing the plasmidial DNA was stored in freezer at −20° C.

The samples, before being prepared for sequencing, were submitted to a digestion reaction using restriction enzymes, in order to confirm the presence of the insert and its size. The digestion reaction were composed 1.5 µL of React 3 enzyme buffer; 0.5 µL of EcoRI (10 U/µL); 5 µL of plasmidial DNA (~10 ng) and 8 µL of ultra pure water, and incubated at 37° C., for 2 h. After this period, aliquots of the reaction were submitted to 1% agarose gel eletrophoresis.

The fragments were sequenced by a ABI Prism 3100 (Applied Biosystems) capillary sequencer, using ABI Prism BigDye terminator cycle sequencing (Applied Biosystems) kit on both orientation of the DNA double strand, using in different reactions and different sequencing experiments, M13 R and F primers. The sequencing reaction was preformed by placing 1.5 µL of DNA from each sample on the plate and 8.5 µL of the reaction mix which was prepared according to the protocol described in the table below.

TABLE 2

Reagents used in the preparation of the reaction mix used for the sequencing reaction.

| Reagents | Volume per reaction |
| --- | --- |
| Ultra pure water | 2.5 µL |
| Save Money | 2.0 µL |

TABLE 2-continued

Reagents used in the preparation of the reaction mix used for the sequencing reaction.

| Reagents | Volume per reaction |
| --- | --- |
| Big Dye V. 3.1 | 2.0 µL |
| Primer - M13 (2 pmol/µL) | 2.0 µL |

The sequencing reactions were conducted using Applied Biosystem thermocycler, under the following conditions: 96° C. for 2 min, 30 cycles of 96° C. for 15 sec; 50° C. for 15 sec, and 60° C. for 4 min. Finally, the reaction for DNA precipitation was performed adding 80 µL of 75% isopropanol to each sample, followed by an incubation of 15 min at room temperature, protected from light, and a centrifugation step of 45 min, at 1.310×g.

The supernatant was discarded and the pellet was washed using 100 µL of 70% ethanol, followed of a centrifugation step of 15 min, at 1.310×g. The supernatant was discarded and, at room temperature and protected from light, the pellet was dried. For the sample application in the sequencing machine, the pellet was ressuspended in 10 µL of hi-formamide, and then, the samples were incubated on the thermocycler at 95° C. for 5 min, in order to cause DNA denaturation. The plate was immediately transferred to ice to avoid DNA reannealing and, after that, taken to the sequencing machine.

Figure 6:
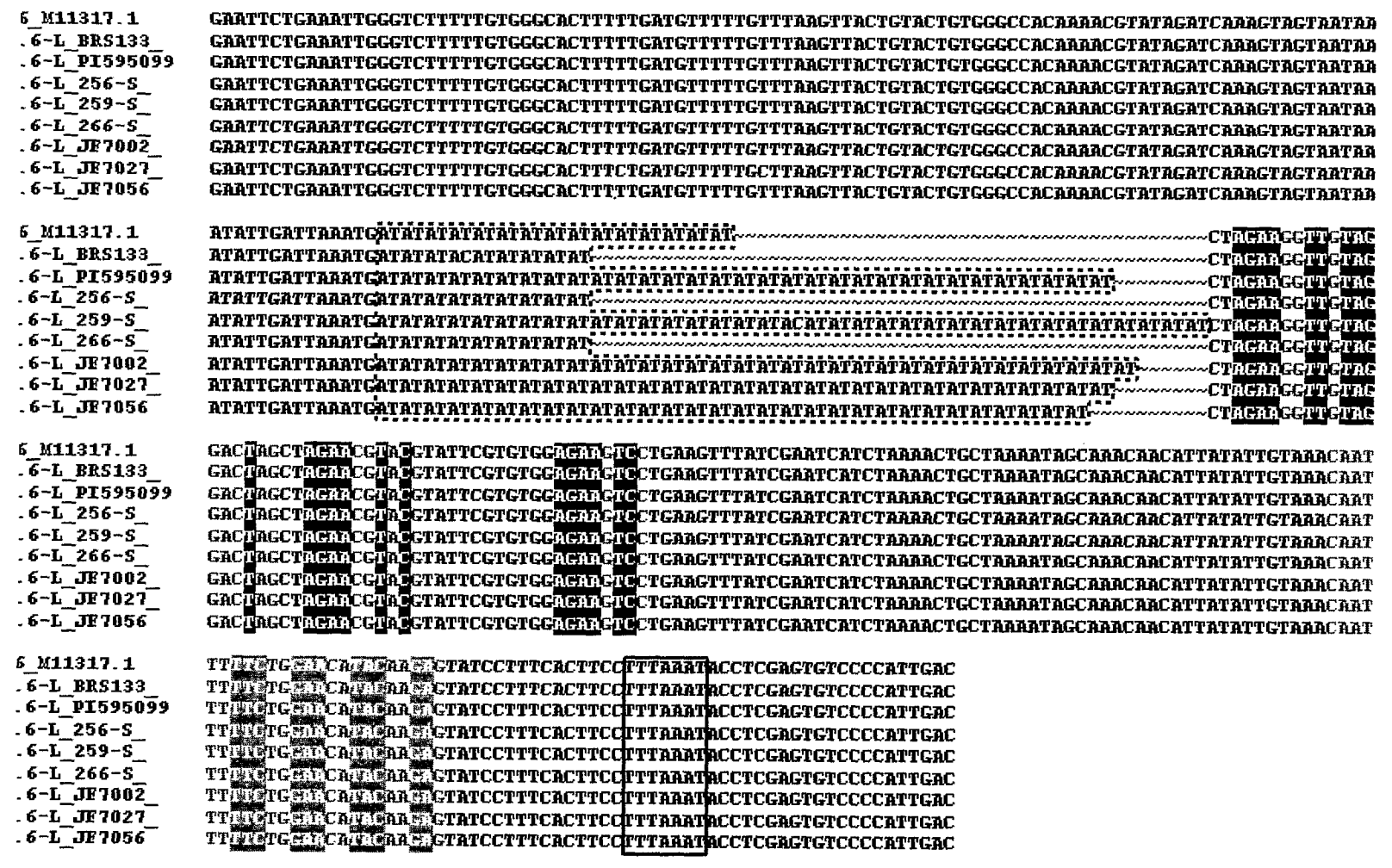

After the sequencing of the promoter region and the complete gene region, a sequence database search of biological sequences was conducted to verify the similarity between the obtained fragment and known DNA and protein sequences (FIG. 6). To accomplish this, the programs BLASTn and BLASTx (Altschul et al. (1997), Nucleic Acids Res. 25: 3389-3402) were used. Alignments of nucleotide sequences (FIG. 7 and FIG. 8) as well as amino acid sequences (FIG. 9) were also performed using appropriated softwares such as Vector NTI Advanced 10.0.1 (Invitrogen Corp.), BioEdit Sequence Alignment Editor and Clustal W.

Example 2: Study of Control of Gene Expression—RPA

The parental genotypes PI595099 (resistant) and BRS133 (susceptible) were chosen for the RPA experiement. From the complete sequence of heat shock protein gene, Gmhsp17 0.6-L (GenBank accession number: M11317), present in soybean, a primer set was designed for the coding region (RPA2_F 5'GAC ATC ATC AAA CAA GAG AA3' (SEQ ID NO: 8) and RPA2_R 5'TCT CTC CGC TAA TCT GAA3' (SEQ ID NO: 2)).

The seed DNA extraction from the analyzed parental samples, the amplification of fragments through PCR, the cloning and the sequencing of the PCR-generated products were performed according to protocols previously described in details in the aforementioned items.

The total RNA from the parental PI595099 (resistant) and BRS133 (susceptible) were extracted from soybean roots submitted to two different treatments: inoculated and non-inoculated with *M. javanica* nematode eggs. The extraction was performed using the Trizol Reagent (Life Technologies) kit. The roots were grinded using a mortar and pestle in liquid nitrogen and transferred to autoclaved falcon tubes and store at the fume hood, containing 20 mL of Trizol. After homogenization, the samples were incubated for 5 min at room temperature (15-30° C.) 0.2 mL of chloroform for each 1 mL of Trizol was added and, after vigorous agitation for 15 sec, the solution was incubated at room temperature (15-30° C.) for extra 3 min. It was followed by a centrifugation step at 12.240×g, for 15 min at 4° C. The liquid phase, that contains the RNA, was transferred to a new falcon tube and precipitated using 0.5 mL of isopropanol for each 1 mL of Trizol initially used. The solution was incubated at room temperature (15-30° C.) for 10 min. A new centrifugation step at 12.240×g, for 10 min, at 4° C., was performed. The pellet formed on the bottom of the tube contains the precipitated RNA. The whole supernatant was removed and the RNA pellet was washed using 75% ethanol (1 mL de ethanol for each 1 mL of Trizol used). The solution was centrifuged at 4.285×g, for 5 min, at 4° C., and, once again, the whole supernatant (ethanol) was removed. 400 µL of DEPC water were added to the pellet in order to dissolve it (if necessary, the temperature can be elevated to 50-60° C. in order to dissolve the pellet). After the extraction, the total RNA was quantified by spectrophotometry; its integrity was verified in 2% agarose gel and, finally, stored in ultrafreezer at −80° C.

Initially, the plasmid containing the fragment of interest was linearized. The reaction containing 30.6 µL of DEPC water, 4 µL of buffer, 1 µg of the purified plasmid, 0.4 µL of BSA and 1 µL of the restriction enzyme ApaI, was incubated at 37° C., for 2 h using a thermocycler. After this period, the plasmid was purified using 1 volume of phenol, mixed using a vortex for 2 min and submitted to a centrifugation step at 11.750×g, for 10 min, at 4° C. Following, the aqueous phase was collected and ammonium acetate ($NH_4OAc$) was added to a final concentration of 0.5 M. Three volumes of cold 95% ethanol were added and the solution was incubated at −20° C. for 1 h. A new centrifugation step at 11.750×g, at 4° C., for 15 min was performed and the supernatant was carefully discarded. The tube was opened; the pellet was dried for 5 min, and, following, ressuspended in 30 µL of DEPC water and stored in freezer at −20° C.

Obtaining Probes

The transcription reaction for obtaining probes was performed using the MAXIScript™ In Vitro Transcription (Ambion Inc.) kit. RNA polymerase T7 and $P^{32}$-labelled phosphate dideoxinucleotide (CTP) were used. Initially, all kit reagents were thaw and kept on ice, with the exception of the Transcription Buffer®, which must be stored at room temperature. The transcription reaction with total final volume of 20 µL was performed in 1.5 mL microtube, at room temperature, according to the protocol described on the table below.

TABLE 3

Reagents used in the transcription reaction of radioactive probes.

| Reagents | Volume per reaction |
| --- | --- |
| DEPC water | 5 µL |
| 10X Transcription buffer | 2 µL |
| 10 mM of ATP | 1 µL |
| 10 mM of UTP | 1 µL |
| 10 mM of CTP | 1 µL |
| 10 mM of GTP | 1 µL |
| Linearized DNA (0.5 µg/µL) | ~5-6 µL |
| [α-$^{33}$P] CTP (800 Ci/mmol, 20 mCi/mL) | 2 µL |
| RNA polimerase + ribonuclease inhibitor | 2 µL |

Following, all reagents were gently mixed in the microtube and the reaction was incubated at 37° C., for 1 h, using a thermocycler. 2 U of DNase I RNase-free was added and the reaction was incubated for 15 min, at 37° C. One volume of gel loading buffer (95% formamide, 0.025% bromophenol blue, 0.025% xylene cyanol, 0.5 mM EDTA, 0.025 SDS) was added to the reaction, the tubes were heated for 3-5 min at 85-95° C., and the whole sample was applied on 5% polyacrylamide gel, urea 8 M, 1×TBE buffer.

A final volume of 25 mL of gel was prepared, using 12.01 g de urea, following, 3.12 mL of 40% Acrylamide: bisacrylamide (19:1) and 2.5 mL of 10×TBE. A small amount of water was also added avoiding exceeding the final volume of the gel. To dissolve the urea, the solution was kept in magnetic stirring system with heater and after was cooled down; transferred to a cylinder and the final volume of gel was completed with DEPC water. 12.5 µL of TEMED was then added and, at last, 156.2 µL 10% ammonium persulphate.

This solution was immediately applied to glass plates and a well comb was placed, allowing polymerization without moving the plates. A pre-treatment of these materials can be performed that consists in washing and treating with RNase AWAY® (Invitrogen—Life Technologies) the glass plates and the eletrophoresis chamber. On the smaller plate 1-3 mL Repel can be applied under the fume hood allowing the plates to dry for 5-10 min. This treatment facilitates the gel removal after the eletrophoresis.

Before proceeding to the eletrophoresis, the plates were cleaned, eliminating the excess of urea and after the removal of the well comb, the wells were washed, with the running buffer, with the aid of a syringe. A 20-30 min pre-run of the gel, using indicated voltage for the chamber, was performed, and following, the samples were applied. An eletrophoresis of approximately 2 h was conducted, at 200-300 volts, according to the size of the probe.

Only full-length probes were gel purified. To accomplish this, after eletrophoresis, the plates were opened, the gel was covered with plastic film, and an autoradiography film marked in order to guide the identification of the bands positions were exposed for approximately 1 h. Following, the film was developed in a dark room submerging it in developing solution for 5 min, removing the excess, submerging it in water for approximately 3 min for a wash and finally in fixing solution for 5 min. The film was then washed in water and air dried. The alignment of the film with the gel was performed in order to localize the position of the full-length transcripts. The areas of interest of the gel were removed and transferred to a microtube containing 350 mL of elution buffer (0.5 M ammonium acetate, 1 mM of EDTA, 2% SDS). The tubes containing the probes were incubated at 4° C., overnight, to maximize the probe recovery, which was stored at 20° C., until the time of hybridization. The kit for labeling the probes provided a positive control for monitoring its quality.

From the control DNA, the linearized pTRIPLEscript plasmid, containing the 250 bp insert of the rat β—actin gene, a probe was synthesized and hybridized to rat liver the total RNA, also provided in the kit. Two control tubes, containing only yeast total RNA, were used to verify the action of the RNase enzyme. This way, the enzyme positive control tube contained RNase and buffer, while the negative control tube contained only buffer without the enzyme.

Sample hybridization and digestion.

Figure 10:
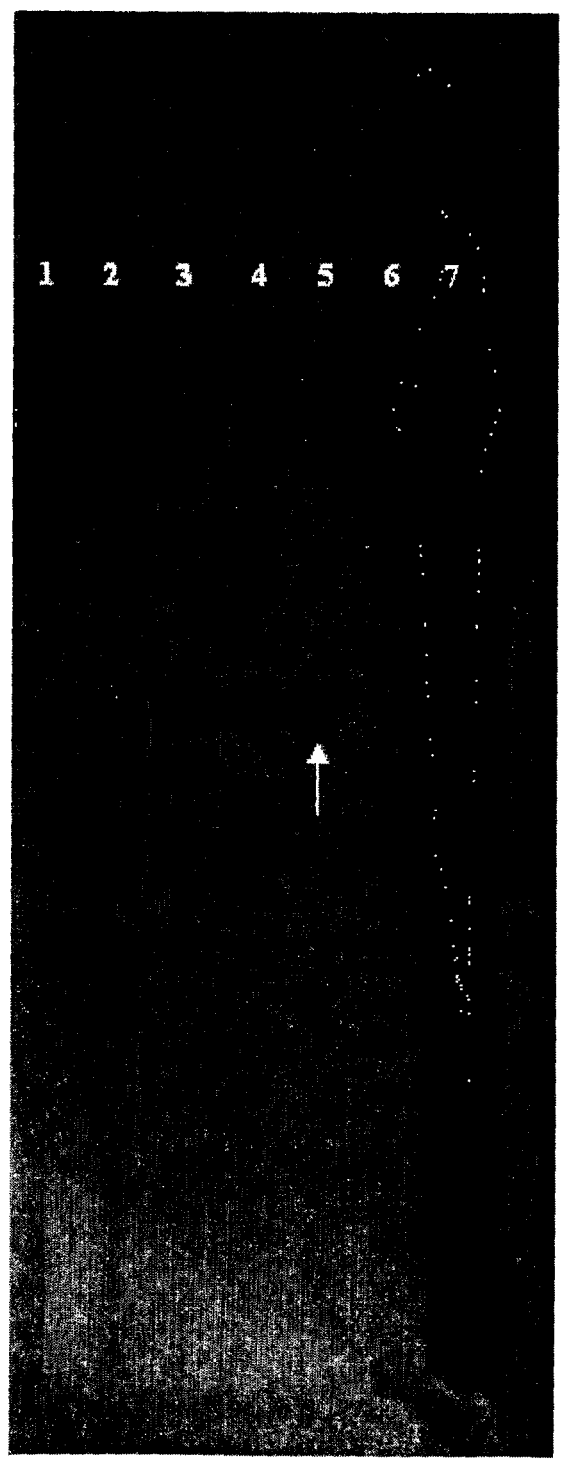
FIG. 10 shows the ribonuclease protection assay performed with a probe (326 pb) constructed from the fragment of the gene Gmhsp17.6-L (access number at the GenBank: M11317), using samples resistant and susceptible to *M. javanica*. The numbers in the upper part are equivalent to the samples used: susceptible parentals (BRS133) and resistant (PI595099) in the non-inoculated (1 and 3) and inoculated (2 and 4) treatments with eggs of *M. javanica*, positive control of kit (5—indicated by the arrow), controls of RNase enzyme, digested probe (6) and not-digested with a RNase (7).

The Ribonuclease Protection Assay (RPA) was conducted using the HySpeed™ RPA—Hygh—Speed Hybridization Ribonuclease Protection Assay (Ambion Inc.) kit. To each microtube, the labeled probe was added (approximately, 100-800 pg of 250 nt or 1-10 fmol or $2-8\times10^4$ cpm with high specific activity) to the total RNA (20 mg). It was also added to the samples 30 mg of yeast total RNA to obtain a final 50 mg/sample. Two other enzyme control tubes were obtained containing 10 mL of yeast total RNA (50 mg) and one tube as probe positive control containing rat liver total RNA. In order to co-precipitate probe+sample, 0.5 M $NH_{40}$ ac and 3 volumes of cold 95% ethanol was added and, after homogenization, the tubes were incubated for 15 min at $-20°$ C. A centrifugation step at maximum speed (minimum of 8.160× g) for 5 min, at $4°$ C., was conducted. The supernatant was removed and the pellet was dried. 10 mL of HySpeed Hybridization Buffer® (pre-heated at $95°$ C.) were added to each sample and the tubes were immediately incubated at $95°$ C. (water bath or thermocycler). To dissolve the pellet, the samples were vortexed for a few seconds and returned to $95°$ C. When the pellet was completely dissolved, the tubes were incubated at $95°$ C. for 3 min and at $68°$ C. for 10 min. The temperature must be maintained at $68°$ C. and the transferring step must be under 30 sec. Initially, the HySpeed RNase digestion Buffer® was thawed, a mix of RNase A/T1 and buffer (dilution of 1:100-1 mL RNase in 99 mL of buffer) was prepared in appropriate volume of 100 mL for each sample and stored at room temperature. 100 mL of mix RNase A/T1+buffer were added to each sample and to the control tubes containing only yeast total RNA, 100 mL of HySpeed RNase Digestion® buffer without enzyme was added to one tube, and the complete mix with enzyme was added to the other control tube. The samples were vortexed and incubated at $37°$ C. for 30 min for digestion. 150 mL of HybSpeed inactivation/precipitation Buffer® was added to the samples which were briefly vortexed and the tubes were incubated in freezer at $-20°$ C. for 15 min. Following the digestion, the samples were centrifuged for 15 min, at maximum speed, at $4°$ C., the supernatant was removed and the pellet ressuspended in gel loading buffer, usually, a volume of 9-10 mL. After pipette homogenization, the tubes were heated for 3-4 min at $90-95°$ C., and quickly transferred to ice to avoid renaturation. The samples were applied to 5% polyacrylamide gel, 8 M urea, diluted in 1×TBE buffer, and an eletrophoresis at 200-300 volts, for approximately 2 h, was performed for separation of the protected fragments. After the eletrophoresis, the standard procedures for film exposition and developing detailed in previously described protocols, were conducted (FIG. 10).

Example 3: Study of Gene Expression—RT-qPCR—Experiment Setting at Greenhouse

For the expression study of the promoter of the gene Gmhsp17.6-L, using the RT-PCR technique, seeds from the materials PI595099, BRS133, 256-S, 259-S, 266-S, JF7002, JF7027 and JF7056 were plated on germination paper at growth chamber and, after eight days, the seedlings were transferred to plastic containers. At green house, these seedlings were infected with juvenile *Meloidogyne javanica* at infecting stage of development J2. The nematode population used was obtained from Centro Nacional de Pesquisa de Soja (Embrapa Soja) and was propagated on soybean plants from the cultivar Doko. The nematode egg extraction from root was obtained by grinding the material using a blender for 30 sec in a 0.5% hypochlorite solution. The roots were washed in water and the eggs were collected using a miniscreen with exclusion size 500. Following, the free eggs suspension were transferred to eclosion chambers set at $26°$ C., and, at every 24 h, the juveniles (J2) were collected and stored in a refrigerator. The juveniles J2 were quantified in a Peters Chamber. With the aid of a pipette, 664 J2/mL per plant were inoculated and at 1, 3 and 6 days pos infection, roots from three soybean plants of each of the eight materials under study were bulk collected and transferred to liquid nitrogen, for the inoculated ones and the non-inoculated with juveniles (control treatment). The roots were stored in ultrafreezer at $-80°$ C., until the beginning of the RNA extraction experiment.

RT-qPCR Primer Design

The primers used for the real time PCR (SoyHspPSC_F 5'GCT GTG TGT CAT TGT CAT CGA A3' (SEQ ID NO: 10); SoyHspPSC_R 5'CAC GGT CTA TTT CTT GCC TAC ATC3' (SEQ ID NO: 11)) were designed with the aid of the Primer Express 2.0 (Applied Biosystems) program, using the sequence pos stop codon (TAA-nucleotide position 884) of the Gmhsp 17.6-L gene (GenBank accession number: M11317). These primers were used to amplify a fragment of approximately 80 bp. The chosen parameters applied to the Primer Express program to design the primers were: amplicon length between 50 bp and 150 bp (120 bp is recommended for RT-PCR), CG content between 40% and 60%, maximum of 4 G bases in tandem, primer Tm (Melting temperature) between $58°$ C. and $60°$ C., maximum difference between Tm of F and R primers of 1 degree Celsius, and up to 4 identical bases in tandem should be avoided. Following, in order to analyze the formation of primer dimers, the program OMIGA were used, observing the existence of a minimum of 6 free bp at the 3' end.

Total RNA Obtaining for cDNA Synthesis

In order to perform real time PCR experiments, total RNA was extracted with Trizol reagent (Invitrogen—Life Technologies). Initially, 1 mL of Trizol per sample was aliquoted in Falcon tubes and heated at $55°$ C. The sample plant tissue was homogenized in liquid nitrogen and 0.1 g was aliquoted in tubes that were maintained in nitrogen. Following, 1 mL of heated Trizol were added to the samples, which were vortexed for 1 min, were quickly spun down and were incubated for 2 min at $55°$ C., followed by incubation on ice for 1.5 h. The samples were centrifuged at $4°$ C., for 20 min, at 16.000×g, the supernatant was transferred to tubes containing 200 µL of chloroform and the residues were discarded. The samples were shaken and incubated at room temperature ($22-25°$ C.) for 2 min, followed by a centrifugation step at 16.000×g, for 30 min, at $4°$ C. The supernatant was transferred to a new tube and it was added ⅓ of the volume of 8 M LiCl. After shaking, the tubes were incubated in freezer at $-80°$ C., for 1 h. In order to thaw the solution, the tubes were maintained for 1-3 min in water bath at $40°$ C., and centrifuged at 16.000×g, at $4°$ C., for 30 min. The supernatant was removed and discarded, avoiding disturbing the pellet which contains the RNA. It was added to each sample 400 µL of 75% ethanol and the tubes were gently inverted. A centrifugation step at $4°$ C. for 5 min, at 16.000×g was performed and the supernatant removed and completely discarded. It was added 100 µL of ultra pure water to the pellet and by gently flicking the tube, the pellet was dissolved (In case the pellet is not quickly being dissolved, an extra 100 µL of ultra pure water can be added, however, the volumes of sodium acetate and isopropanol at the next step should be doubled). Next, 10 µL of sodium acetate (3 M) and 100 µL of isopropanol were added and the tubes were gently inverted. The samples were incubated at $-80°$ C., for 30 min, and transferred to water bath at $37°$ C. for 1-3 min, and centrifuged at 16.000×g, at $4°$ C., for 15 min. The supernatant was removed, 400 µL of 70% ethanol were added and the tubes were once again centrifuged 16.000×g, at $4°$ C., for 15 min. The supernatant was removed and discarded and, for 10 min, the pellet was dried at the bench. Finally, 50 µL of ultra pure water (or 100 µL, if the pellet is not quickly dissolved) was added and both the pellet and the solution were heated at 37° C., for 10 min, to facilitate the dissolution of the pellet. The RNA was quantified and stored in freezer at −80° C. For the reverse transcription reactions, the RNA was diluted and the cDNA synthesis was performed, using the reverse transcriptase enzyme (Moloney Murine Leukemia Virus—M-MLV). This way, 1.5 mg of total RNA was aliquoted in microtube, it was added DEPC water to a final volume of 9 mL, 6 mM of random primer was added to the reaction, followed by incubation at 80° C., for 3 min. After this period, the tubes were cooled down on ice and 14 mL of the mix was added to the samples. The mix was prepared according the protocol described on the table below.

TABLE 4

Reagents used in the mix preparation for cDNA synthesis

| Reagents | Volume per reaction |
| --- | --- |
| 5X first strand buffer 6 mL dNTP (2.5 mM) | 4 mL |
| DTT (0.1M) | 2 mL |
| Reverse transcriptase enzyme | 2 mL |

The reactions were incubated using a thermocycler at 37° C., for 1 h, followed by a step of 10 min, at 65° C. The cDNA was stored at −20° C.

RT-qPCR

The PCR reactions were performed using the thermocycler 7300 Real Time System (Applied Biosystem), using the Platinum® SYBER® Green qPCR SuperMix UDG (Invitrogen—Life Technologies) kit, according to the manufacturer's instructions. As recommended by Applied Biosystems, an amplification efficiency curve was performed for the primer sets of the target gene Gmhsp 17.6-L and the endogenous control gene rRNA 18S (GenBank accession number: X02623.1), used for the samples normalization. The experiment plate was set with samples in triplicates for both genes. The curve provided a slope, used to calculate the amplification efficiency of the primers, which must be similar and close to 100% (value 1) for both genes. The amplification reactions for relative quantification were performed using a bulk of cDNA from the three days of harvest for each of the analyzed samples. It was performed, in separate experiments, two real time PCR experiments for the parental samples and two for the population samples. The parental lines BRS133 and PI595099 and the six resulting individuals from the susceptible populations, 256-S, 259-S and 266-S, and resistant, JF7002, JF7027 and JF7056, were analyzed for the nematode-inoculated treatment and non-inoculated treatment. The reaction were performed in triplicates and composed of 8.0 µL of ultra pure water, 0.5 µL of ROX, 12.5 µL of SYBER® Green qPCR SuperMix UDG and 2 µL of bulk cDNA (~1.5 µg). The cycling parameters for the amplification reactions were: 50° C. for 2 min; 95° C. for 2 min; followed by 45 cycles of 95° C. for 15 sec, 60° C. for 30 sec and 72° C. for 30 sec, the data was collected at the extension step (72° C.). After the relative quantification was concluded, in order to verify the formation of primer dimers, inespecific amplifications and possible errors and contaminations, a dissociation curve was performed. The interpretation of the RT-PCR-generated data was performed using the SDS—Sequence Detection Systems (Applied Biosystems) software.

Figure 11:
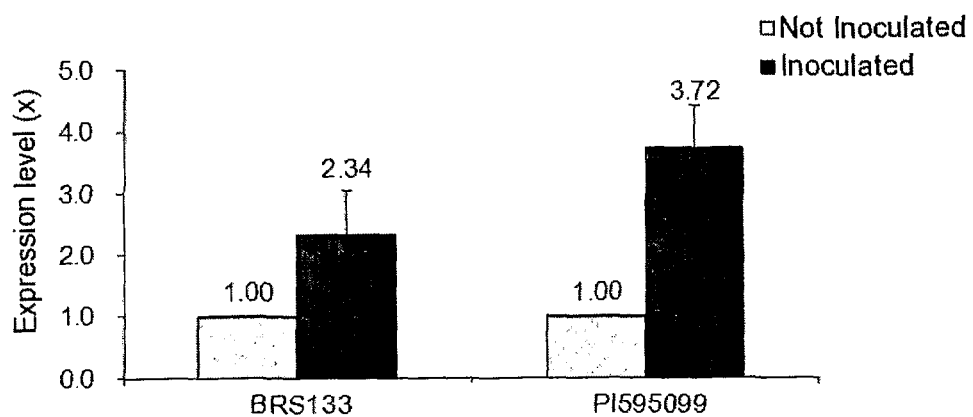
FIG. 11 shows the relative quantification of the gene Gmhsp 17.6-L in the resistant (PI595099) and susceptible (BRS133) parentals, in the treatments: inoculated and non-inoculated with the cyst nematode *M. javanica*. The data was obtained by PCR in real time, with the primers SoyHSP PSC F and SoyHSP PSC R, designed with the program Primer Express® Software v20, using the complete sequence of the gene available at the GenBank (access number: M11317). Quantification was performed using the $2^{-\Delta\Delta Ct}$ method. The gene rRNA 18S was used as normalizer and as non-inoculated samples as gauges. The samples were amplified in triplicate in three independent runs using the SYBR methodology.
Figure 12:
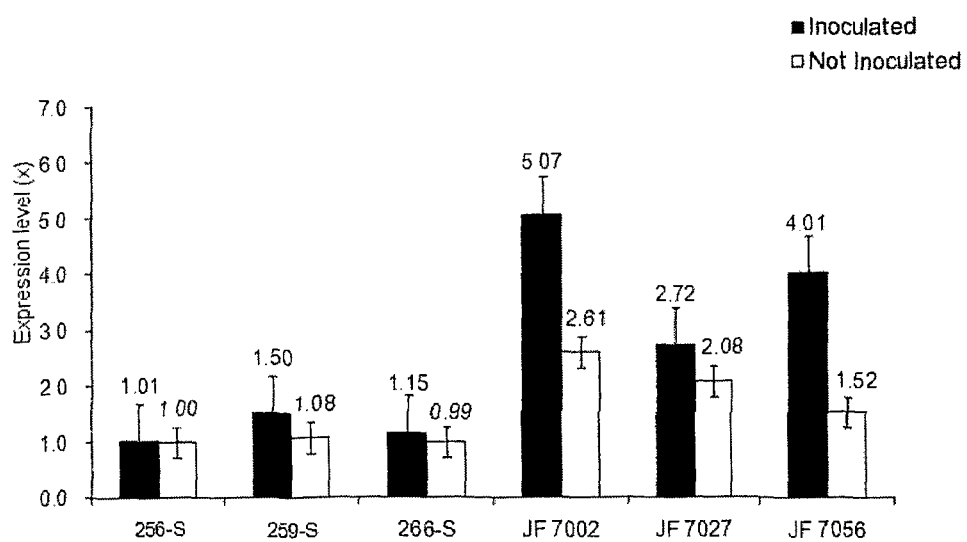
FIG. 12 shows the relative quantification (x) of the gene Gmhsp 17.6-L in individuals of the susceptible population, 256-S, 259-S and 266-S; and resistant, JF7002, JF7027 and JF7056, in the treatments: inoculated and non-inoculated with the cyst nematode M. javanica. The data was obtained by PCR in real time with the primers SoyHSP PSC F and SoyHSP PSC R designed with the program Primer Express® Software v20, using the complete sequence of the gene available at the GenBank (access number: M11317). Quantification was performed using the $2^{-\Delta\Delta Ct}$ method. The gene rRNA 18S was used as normalizer and non-inoculated samples 256-S as gauge. The samples were amplified in triplicate in three independent runs using the SYBR methodology.

In these analyses, the calculation of the relative gene expression (RQ) was performed individually, comparing sample in separate, for nematode-inoculated and non-inoculated treatments, using as calibrator (value 1) the non-inoculated sample. The RQ value was calculated using the ΔCt method. This way, the level of gene expression (RQ) is calculated by subtracting the Ct of the target sample of each treatment with the endogenous control Ct, generating the Δct. This value is subtracted from the ΔCt of the control sample (calibrator—value 1), resulting in the value of ΔΔCt. The RQ is obtained through the formula 2—ΔΔCt, in which 2 corresponds to the sum of the target gene efficiency (100%=1) and of the endogenous control (100%=1) obtained at the 100% efficiency curve (Livak and Schmittgen (2001), Methods 25: 402-408). The efficiencies of the target gene and endogenous gene must be close to 100%, but it is not necessary, they can be lower, however, they must be close. And, in this case, the value at formula 2—AACt, is substituted by the sum of the efficiencies of the target gene and the endogenous gene. For the analysis of the parental lines BRS133 and PI595099 in the treatments of inoculation and non-inoculation (FIG. 11) with the gall nematode *M. javanica*, the non-inoculated sample PI595099 was used as calibrator (value 1x) and, for the analysis of the susceptible populations (256-S, 259-S and 266-5) and for the resistant ones (JF7002, JF2027 and JF7056) (FIG. 12), the non-inoculated susceptible sample 256-S was used as calibrator sample. This material was chosen due to the fact that in the sequencing of the promoter region of the Gmhsp17.6-L gene, it presented a lower number of AT(n) insertions.

Example 4: Expression Cassette Constructs Containing Different Sizes of AT(n) Insertions in the Promoter Region of the Gmhsp17.6-L Gene Once verified that the resistant individuals present a higher number of AT(n) insertions in the promoter region of the Gmhsp17.6-L gene and that these individuals, when submitted to RT-PCR, present high levels of this gene expression, when inoculated with the gall nematode *M. javanica*, it was decided to have expression cassettes constructed containing different number of AT insertions in the promoter region of the Gmhsp17.6-L gene. The objectives of utilization of these constructs were to observe if these promoters, with AT(n) insertions, could induce the expression of other genes and, also, evaluate the response of those genes, their activation or not upon different stresses. The cassettes were used to transform, using particle bombardment, soybean embryos from nematode-susceptible cultivars, BRS133 and Pintado. In the obtained construct, the promoter of the Gmhsp17.6-L gene is positioned prior the Gus gene which, after submission of the embryos to different stresses, had its expression detected through histochemical assay.

Figure 13:
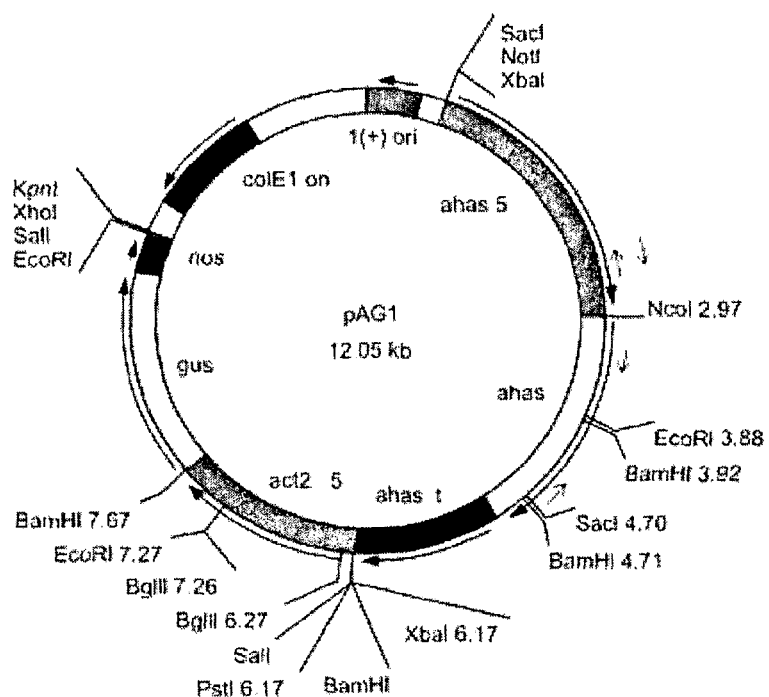
FIG. 13 shows a schematic model of the plasmid pAG1, illustrating the Gus reporter gene, which encodes the enzyme β-glucuronidase, the gene Ahas and the promoter act2. The restriction map is also presented.
Figure 14:
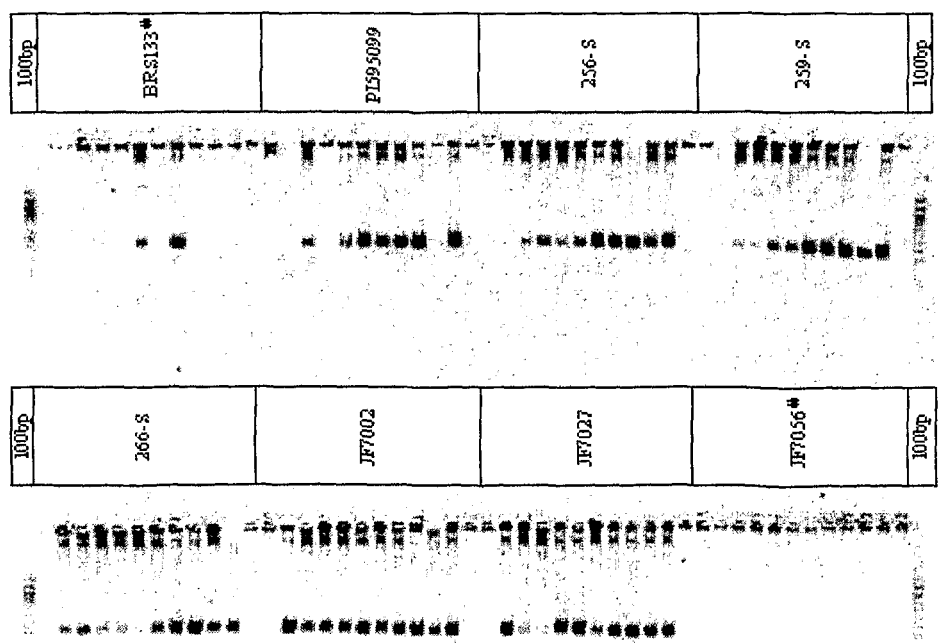
FIG. 14 shows amplifications via PCR of the promoter region of the gene Gmhsp17.6-L, of all the constructs of expression cassettes obtained with the materials studied: BRS133, PI595099, 256-S, 259-S and 266-S, JF7002, JF7027 and JF7056. The reactions were carried out using the primers pSoyHSPPstI_F and pSoyHSPBamHI_R which amplify a fragment of 363 pb and, subsequently separated by electrophoresis in agarose gel 1.0%. The amplification reactions of the samples BRS133 and JF7056 evaporated during PCR.
Figure 15:
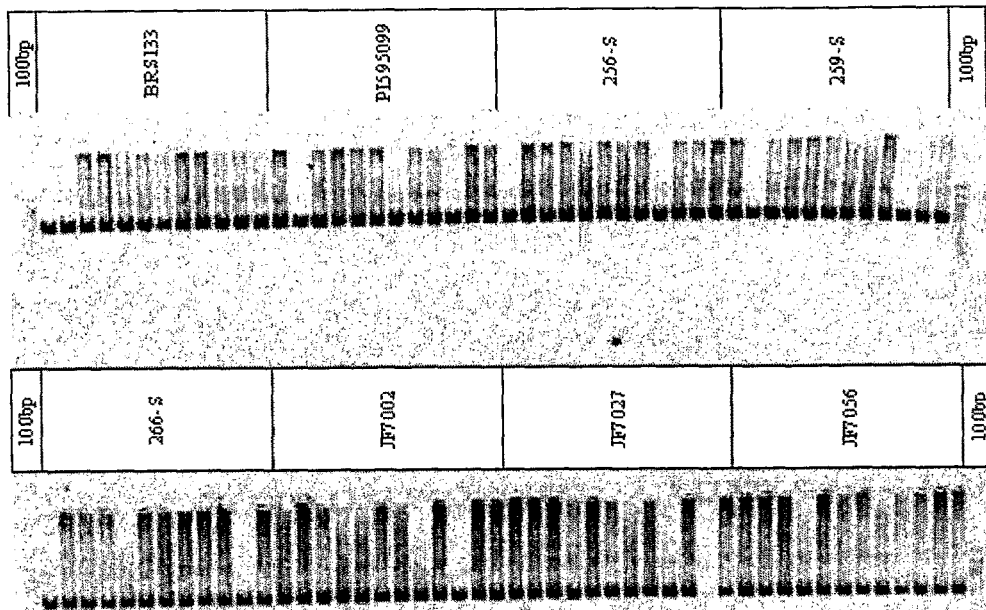
FIG. 15 shows amplifications via PCR of part of the gene Ahas, present in the plasmid pAG1, of all the constructions of expression cassettes obtained with the materials studied: BRS133, PI595099, 256-S, 259-S, 266-S, JF7002, JF7027 and JF7056. The reactions were carried out using the primers Ahas1_F and Ahas2_R which amplify a fragment of 654 pb and, subsequently, separated by electrophoresis in agarose gel 1.0%.
Figure 16:
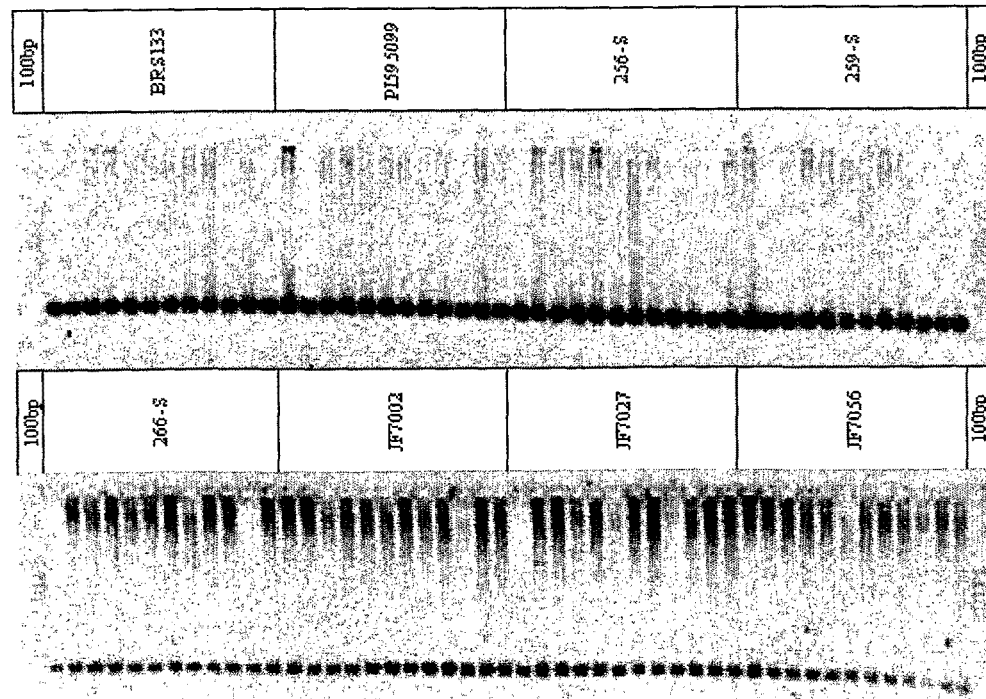
FIG. 16 shows amplifications via PCR of terminal region Nos, present in the plasmid pAG1, of all constructs of expression cassettes obtained with the material studied: BRS133, PI595099, 256-S, 259-S, 266-S, JF7002, JF7027 and JF7056. The reactions were carried out using the primers Nos1_F and Nos3_R which amplify a fragment of approximately 200 pb and, subsequently, separated by electrophoresis in agarose gel 1.0%.

Expression cassettes containing the promoter region of eight analyzed samples, BRS133, PI595099, 256-S, 259-S and 266-S, JF7002, JF7027 and JF7056, were obtained, being 96 cassettes on total (12 of each of the materials). However, only two constructs were used in the next step of the study, the cassette pAG1/promotorGmhsp_BRS133, containing the amplified promoter region from the susceptible parental BRS133, with the fewer number of insertions, which is AT(9), and the cassette pAG1/promotor-Gmhsp_JF7027, containing the amplified promoter region from the individual from the resistant population JF7027, with AT(32). The plasmid pAG1 was chosen as template for construction of the expression cassettes. The designed strategy was removal of the act2 promoter from actin gene present in the plasmid and insertion of the amplified promoters from the materials to be analyzed, which are susceptible parental line BRS133 and the individual of the resistant population JF7027. This plasmid also presents the reporter gene Gus, which codes for the β-glucuronidase enzyme, which allows by visualization in the transgenic embryos, through histochemical assay, if the transformation process using those cassettes was successful. The plasmid pAG1 also contains the promoter (ahas 5), the coding sequence (ahas) and the terminator (ahas t) of the als/ahas gene, which codes for the enzyme acetolactate pyruvate lyase (AHAS)-acetolactate synthase (ALS) from *Arabidopsis thaliana* which due to a mutation in the position 653, confers resistance to herbicides Imidazolinones, class in which the herbicide Imazapyr (2-[4,5-dihydr-4-methyl-4-(1-methylethyl)-5-oxo-1H imidazol-2-yl]-3-pyridinecarboxylic) belongs to (Tu et al. (2004), Weed control methods handbook; London: Academic). This way, this gene enables, after transformation, the selection of positive plantlets in media containing the herbicide. FIG. 13 present the plasmid map. In order to develop this strategy, a plasmidial DNA extraction was performed, using the Wizard Plus Maxipreps DNA Purification System (Promega) kit. This way, a single colony was inoculated in 2-5 mL of LB media, containing the antibiotic ampicillin (0.5 mg) and incubated at 37° C., for 8 h, rotating at 200 rpm (pre-inocule). 1 mL of the pre-inocule was transferred to 500 mL of LB/ampicillin media and it was incubated at 37° C., for 12 h to 20 h, rotating at 200 rpm. The cells were aliquoted in 250 mL tubes and centrifuged at 5.000×g for 10 min, at room temperature, the supernatant was discarded and the pellet was completely ressuspended in 15 mL of Cell Ressuspension Solution (50 mM Tris-HCl pH 7.5, 10 mM de EDTA, 100 µg/mL de RNase A). 15 mL of Cell Lysis Solution (0.2 M NaOH, 1% SDS) was added, mixed by inversion and the solution was incubated for 20 min at room temperature. Following, 15 mL of Neutralization Solution (1.32 M of potassium acetate, pH 4.8) were added, the solution was mixed by inversion, leading to the formation of a white flake and the lysate becoming less viscous. The precipitated material contains genomic DNA, proteins, cell debris and SDS. A centrifugation step at 14.000×g for 15 min, at room temperature was conducted and the supernatant was filtered in a cylinder containing Whatman 1 filter paper. The volume was measured, transferred to a 50 mL centrifuge tube and 0.5 volume of isopropanol at room temperature was added, mixing by inversion. A new centrifugation step at 14.000×g, for 15 min, at room temperature was performed, the supernatant was discarded and the pellet was ressuspended in 2 mL of TE buffer. To the solution containing the DNA, it was added 10 mL of Wizard Maxipreps DNA Purification Resin®, and the mixture of resin+DNA was transferred to a Maxicolumn connected to a vacuum pump. The vacuum was applied, 25 mL of Column Wash Solution (80 mM potassium acetate, 8.3 mM of Tris-HCl pH 7.5, 40 pM EDTA, 55% ethanol) was added and the vacuum was once again applied. 5 mL of 80% ethanol were applied to the Maxicolumn, the vacuum was applied and, after the whole volume of ethanol was passed through the column, the vacuum was maintained for an extra 1 min. The Maxicolumn was then transferred to a 50 mL falcon tube and centrifuged at 1.300×g, for 5min. The vacuum was applied for an extra 5 min in order to dry the resin. Finally the Maxicolumn was transferred to a provided tube from the kit and 1.5 mL of pre-heated water at 65° C.-70° C. was added to the column. After 1 min has passed, a centrifugation step 1.300×g, for 5 min at room temperature was performed to elute the DNA. After extraction, the plasmidial DNA was quantified and its integrity was verified in 1% agarose gel. For act2 promoter excision (~1000 bp), two restriction enzyme digestions were conducted. In the first step, pAG1 was submitted to double digestion with enzymes PstI and NotI. This digestion resulted in two fragments of approximately 5.500 bp (corresponding to the promoter-ahas 5, the coding sequence-ahas and the terminator-ahas t of the als/ahas gene) and 6.500 bp (corresponding to the Gus gene, act2 promoter and the plasmid backbone, Ori and Nos). The digestion reaction was composed of 10 µL of plasmidial DNA (~1.5 µg), 2 µL of React 2 buffer, 5.0 µL of PstI enzyme (10 U/µL) and 3 µL of ultra pure water. The tube was incubated at 37° C., for 2 h, using a thermocycler. After this period, an extra 2 µL of PstI enzyme (10 U/µL) was added to the solution and it was incubated at 37° C., for 2 h, using a thermocycler. In the same microtube, the reaction using NotI was performed, adding 3.5 µL of NotI enzyme (10 U/µL), 1.5 µL of React 2 buffer and 2 µL of NaCl 1 M. Followed by new incubation for 2 h at 37° C., after this period, an extra 2 µL of NotI enzyme was added. The reaction was maintained overnight using a thermocycler at 37° C. The pAG1 digested fragments were separated in 0.8% agarose gel, and gel extracted using the PureLink™ Quick Gel Extraction (Invitrogen) kit, according to the protocol described in the aforementioned item. In the second step of the digestion, the bigger fragment, of 6.500 bp, was digested with the restriction enzyme BamHI, for excision of the act2 promoter. The reaction was composed of 0.5 µL of BamHI enzyme, 15 µL of React 3 buffer, 12 µL of the DNA digested fragment and 1 µL of ultra pure water. Using a thermocycler, the microtube was incubated for 2 h, at 37° C. After this period, an extra 0.5 µL of BamHI enzyme were added and the reaction was once again incubated at 37° C., overnight. The fragments were separated in 0.8% agarose gel and the bigger fragment (corresponding to the Gus gene, and plasmid backbone, Ori and Nos) were gel purified, using the PureLink™ Quick Gel Extraction (Invitrogen) kit according to the manufacturer's instructions. In order to obtain expression cassette constructs containing different amplified promoters from the parental line BRS133 and from the resistant individual JF7027, a ligation reaction was performed mixing 11 µL of ultra pure water, 2 µL (~10 ng) of the Ahas fragment, 1 µL (~10 ng) of the Gus fragment, 1 µL (~10 ng) of the purified band from the Gmhsp17.6-L promoter from the respective tested samples, 4 µL of ligase buffer and 1 µL of T4 ligase enzyme. The reaction was incubated overnight, at 14° C. The promoter region fragments from the two selected samples were amplified from genomic DNA using primers pSoyHspPstI_F (5'GGG CTG CAG GAA TTC TGA AAT TGG GTC TTT TTG3' (SEQ ID NO: 12)) and pSoyHspBamHI_R (5'CCC GGA TCC AAT GGG GAC ACT CGA GGT ATT3' (SEQ ID NO: 13)). The restriction sites designed and synthesized in the primers allowed the cloning of promoters of the Gmhsp17.6-L gene in the correct orientation in the same position in which the act2 promoter was previously located. According to previously described protocols, *E. Coli* cells, DH10 B strain, were eletroporated using the ligation reaction of the cassettes and grown in LB media, overnight, at 37° C. From the obtained colonies, a series of PCR-amplifications, using specific primers, and digestion reactions using restriction enzymes were performed in order to verify the cloning of the construct was successful. After this step to prove the success in obtaining the expression cassettes, FOR reactions using specific primers for the promoter region of the Gmhsp 17.6-L gene, for the Ahas gene, (654 bp) (Ahasl_F 5'ACT AGA GAT TCC AGC GTC AC3' (SEQ ID NO: 14); Ahas2_R 5'GTG GCT ATA CAG ATA CCT GG3' (SEQ ID NO: 15)) and for the Nos terminator (NosI_F 5'GAA TCC TGT TGC CGG TCT TG3' (SEQ ID NO: 16);

Nos3 R 5'TTA TCC TAG TTT GCG CGC TA3' (SEQ ID NO: 17)) of the pAG1 plasmid, were conducted using all obtained samples. FIGS. 14, 15 and 16 show, respectively, amplifications of the promoter region of the Gmhsp17.6-L gene, parts of the Ahas gene and the Nos region, of 12 samples of each of the expression cassettes obtained.

Example 5: Study of transient expression or GUS (β-Glucuronidase) Activity

Obtaining Transgenic Plants Through Particle Bombardment

In order to obtain transgenic plants transformed with expression cassettes, pAG1/promotorGmHSP_BRS133 and pAG1/promotorGmHSP_JF7027, initially, a plasmidial DNA extraction was performed, according to previously described protocol. This procedure yielded a great quantity of plasmidial DNA sufficient to be used in the transformation process through biobalistic, gene gun method or particle bombardment. In this process, the introduction of the genetic material in plants is performed using microparticles, usually made from gold or tungsten, with diameter between 0.4-2.0 mm, coated with exogenous DNA. The particles were coated with the DNA molecules of interest, accelerated and shot at high speed due to a shock wave caused by a helium gas discharge under high pressure. When they hit the target cell or tissue, penetrating through the cell wall and the plasmatic membrane without disrupting them (Klein et al. (1987), Nature 327: 70-73), the exogenous DNA must dissociate from the microparticles by the action of the cellular liquid and be integrated to the plant genome. After being cultivated and regenerated in vitro, these transgenic tissues or cells will generate genetic modified plants (Brasileiro and Aragão (2001), Plant Biotechnol J. 3(3):113-121; Rech et al. (2008), Nat Protoc 3:410-418).

Seed Decontamination

Soybean seeds from the cultivars BRS133 and Pintado, both susceptible to the gall nematode, were used. After being weighted, the seeds were decontaminated in 70% ethanol for 10 min, followed by immersion in 1% sodium (V/V) for 20 min. In a laminar flow hood, the seeds were washed three times with autoclaved distilled water and embedded in water at double the volume of the seeds, being kept immersed for hydration for a period of approximately 16 h-18 h.

Embryo Isolation and Preparation of Support Plates for the Bombardment.

With the dehumidifier and the air conditioner on to lower room humidity, the embryos where isolated from the hydrated seeds. With the aid of sterile forceps and surgical blades, the seeds were incised and the embryonic axis removed and transferred to Petri dish containing distilled water to avoid drying. Following, with the aid of a stereomicroscope, the leaf primordia were excised, exposing the apical meristem region. The embryos were transferred to filter paper in a laminar flow hood to remove the water excess, which can lower the transformation efficiency behaving as a barrier to the particle, which will refract. For the bombardment, a centralized circle of 16 mm of diameter (death zone) was designed in small Petri dishes containing MS media (Murashige and Skoog Salt), 3% of sucrose and 0.8% of phytagel, pH 5.7, using a sterile forceps, sulcus were obtained outside the death zone. The embryos were positioned in the plates at the sulcus with the aid of a stereomicroscope, with the apical meristem region facing up. The carrier membrane support and the support cylinder were sterilized by fire and four rupture membrane set were separated and maintained immersed in isopropanol until utilization. The carrier membranes were assembled in their support.

Sterilization and Washing of the Tungsten Microparticles

In a microcentrifuge tube, 60 mg of M 10 tungsten microparticles were weighted, which is sufficient material for approximately 100 shots. To the microparticles, 10 mL of 70% ethanol were added; the solution was homogenized vigorously and kept on an agitator for 15 min in a speed sufficient enough to keep the movement. A centrifugation step at 15.000 g, for 5 min, was performed, and to avoid disturbing the settlement of the microparticle, with the aid of a micropipette, the supernatant was removed and discarded. 1 mL of sterile distilled water was added to the tube, the mixture was homogenized vigorously using an agitator and centrifuged once again at 15.000 g, for 5 min. The supernatant was discarded and the washing procedure was repeated twice. After the last wash and discard of the supernatant, the microparticles were ressuspended in 1 mL of 50% glycerol (V/V).

DNA Coating of the Tungsten Microparticles

In a 1.5 mL microcentrifuge tube, 50 μL of the microparticle suspension were aliquoted and submitted to a sonicator, for 15 min, for homogenization, avoiding, this way, the microparticles agglomeration and enabling a uniform precipitation. DNA equivalent to a minimum of 6 μg were added to the suspension, which was gently homogenized, with the aid of a micropipette. 50 μL of $CaCl_2$ (2.5 M) was added to the solution and, after gentle homogenization, 20 μL of spermidin were added. After another homogenization, the solution was incubated for 10 min, at room temperature, under gentle rotation, in an adapted tube agitator. The tubes were spun down for 10 sec at maximum speed, the supernatant was removed and discarded, carefully, to avoid ressuspension of the microparticles. 150 μL of 100% ethanol was added; the solution was vigorously homogenized and centrifuged once again, for 10 sec, at maximum speed (spin). The supernatant was removed and the washing procedure was repeated once more. After the discard of the supernatant, in the last wash, 24 μL of 100% ethanol were added to the sample which was vigorously homogenized. Finally, aliquots of 3.2 μL of suspension were applied to the central region of each carrier membrane previously positioned on the membrane support. Each precipitation is sufficient to prepare 6 carrier membranes containing the microparticles coated with DNA. After microparticle application, the membranes were stored immediately on plate containing silica gel and were maintained in a dissecting chamber because the DNA-coated microparticles exposition to conditions of relative air humidity above 50% enables agglomeration, resulting in the reduction of the frequency of the exogenous gene expression.

Use of Gene Gun and Bombardment Experiment

The shots were targeted to the meristematic region of soybean seed embryos from cultivars BR133 and Pintado, both susceptible to the gall nematode, according to the protocol developed by Aragão et al. (Crop. Sci. 42: 1298-1302 (2002)), with few alterations. Prior the bombardment, the laminar flow hood was cleaned with 70% ethanol and sterilized with UV light for 15 min. The retention screens, the Petri dishes containing the embryos, the rupture membranes in set of four and immersed in isopropanol, and the carrier membranes containing exogenous DNA were maintained close to the operator. The valve of the helium gas cylinder was opened and the pressure was set at 1.200 psi. Following, the rupture membrane set (300 psi/membrane) was positioned in the far end of the high pressure helium gas chamber, the sealing screw was tightened, and the high pressure chamber was inverted to fit the vacuum chamber. The plates containing the material to be bombarded were positioned and, on the support cylinder, the retention screen and the carrier membrane support, containing the DNA-coated microparticles, were also positioned. Carefully, the support cylinder was positioned and the vacuum chamber was closed. The valve to allow the vacuum inside the chamber was slowly opened, until the pressure of 27 pol/Hg was reached, and at this time this valve was closed. The valve that allows helium gas inside the high pressure chamber was opened and, when the rupture membrane presented bending due to the presence of helium gas, the shot was performed, by pushing the trigger. After the shot, this valve was closed, while the valve that releases the helium gas from the high pressure chamber was opened. Following, the valve that releases the vacuum was slowly opened and the plate containing the embryos that were bombarded was removed from the equipment. At each bombardment, these procedures were repated. After each bombardment, most part of the embryos were transferred to different plates and submitted to abiotic and biotic stresses. Some embryos were, however, transferred to plates containing MS media supplemented with BAP 5 mg/mL (benzilaminopurine), 3% of sucrose 0.6% of agar and pH 5.7, in which were maintained for approximately 18 h protected from light, at 28° C., for regeneration induction.

Selection of Transgenic Embryos

The distinction between transgenic cells and non-transgenic cells can be performed through the introduction in the plant genome, separately or linked to the gene of interest in the same transformation vector, selection genes, which express a protein with enzymatic activity. According to the mode of action, the marker genes are classified as genes that confer resistant to antibiotics, genes that confer resistance to herbicides and marker genes with positive selection (Brasileiro and Dusi (1999), In: TORRES, A. C.; CALDAS, L. S.; BUSO, J. A. Ed. Cultura de tecidos and transformagão genética de Plantas. Brasília: Embrapa-SPI/Embrapa-CNPH, 1999. p. 679-735. v.2). The gene ahas belongs to the class of those which confers resistance to herbicides. This gene codes for a modified form of the acetohydroxil acid synthase (AHAS) enzyme, also known as acetolactate synthase (ALS). A mutation in the position 653 of the sequence resulted in a substitution of a serine by a asparagine, leading to a modified enzyme and that is not recognized by the herbicide class imidazolinones. Meristematic cells transformed with this gene are selected in the presence of the herbicide Imazapyr, in a process based on the systemic translocation of selective molecules to the meristematic regions and inactivation of the endogenous AHAS enzyme. Because the selective agent is localized in the apical meristem, the non-transgenic cells die and the survival of the transgenic cells which will develop into a plant is favored (Aragao and Brasileiro (2002), J. P. Physio, 14 (1)). This way, after the regeneration, some embryos were transferred to plastic cups containing the selective media MS, 3% of sucrose, 0.15 µM of Imazapyr herbicide, 0.8% of agar and B5 vitamin, pH 5.7, and grown for approximately 45 days on growth chamber, at 28° C., in a 16 h photoperiod, light intensity of 50 µmols m-2s-1 and relative humidity above 80%. The regenerated plantlets were, then, transferred to plastic cups containing sand:vermiculite (1:1) that were autoclaved and humidified with nutritive solution at pH 6.6. Later, the cups were covered with plastic bags, for acclimatization, and irrigated with nutritive solution according to necessity, grown on growth chamber for an extra 28-30 days. After this period of acclimatization, the plastic bags were removed so the plants could normally develop, until harvesting of samples for molecular analysis and identification of positive plants through PCR technique, using specific primers, was possible.

Experiments Using, Transgenic Embryos Submitted to Different Stresses

Embryos from the soybean cultivars BRS133 and Pintado, susceptible to the gall nematode and transformed with different expression cassettes, containing the promoter region of the Gmhsp17.6-L gene amplified from the parental susceptible line BRS133 (S—pAG1/promotor-GmHSP_BRS133) and from the individual from the resistant population JF7027 (R—pAG1/promotor-GmHSP_JF7027), were submitted to biotic stress, in this case, inoculation with juvenile J2 of *M. javanica*, and abiotic stress, such as heat, cold, salinity and dehydration (drought). Non-transgenic embryos (CN—negative control) and embryos transformed with only the pAG1 plasmid (CP—positive control) were submitted to the same treatments. The heat stress was applied, maintaining the embryos 25° C. (room temperature), 35° C. and 45° C. (in hothouse). Temperatures of 4° C. (refrigerator) and 15° C. (hothouse) were used in the cold stress. These stresses were applied with the embryos in solution, at time points of 2 h, 4 h and 24 h. The dehydration (drought) was performed in hothouse at 37° C., maintaining the embryos on filter paper, at time points of 2 h, 4 h and 6 h. For the salinity stress, the embryos were kept for 24 h at concentration of NaCl of 200 mM and 400 mM. The biotic stress was performed by maintaining the embryos in solution containing nematodes at J2 developmental stage (2.000 to 3.000 J2 per mL), for periods of 24 h, 48 h and 72 h. FIG. 17 demonstrates how the stress were applied.

Figure 18:
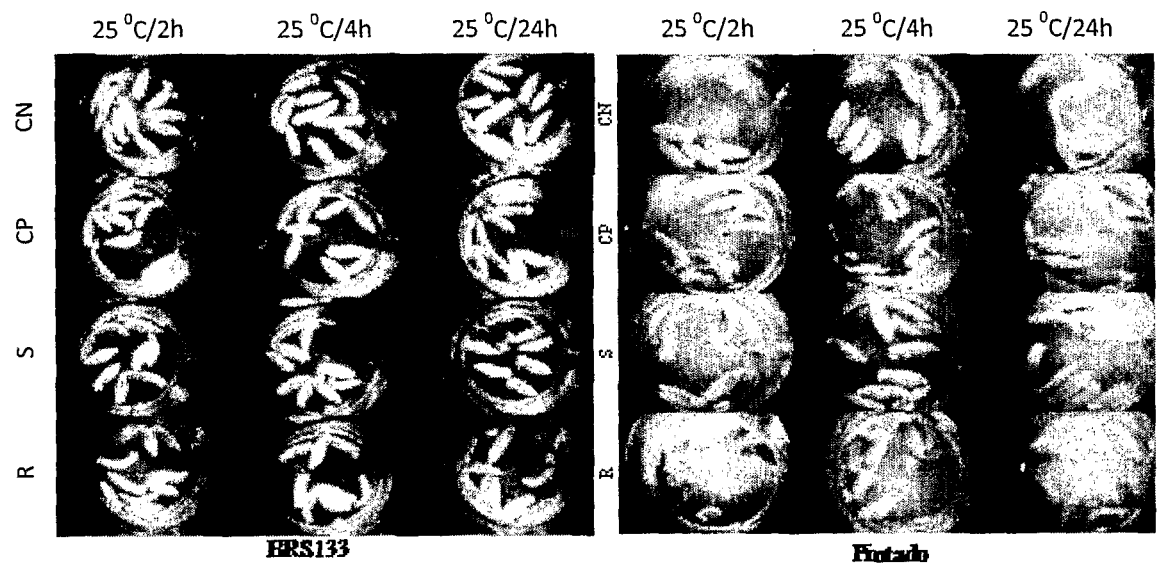
FIG. 18 shows the histochemical test performed with embryos of soybean cultivars BRS133 and Pintado (speckled), susceptible to the cyst nematode M. javanica, transformed by biobalistics, with the expression cassettes pAG1/promotorGmhsp_BRS133 and pAG1/promotorGmhsp_JF7027, and submitted to heat stress at a temperature of 25° C., for periods of 2 h, 4 h and 24 h. Blue dots indicate positive reaction. CN—negative control, embryos not transformed; CP—positive control, embryos transformed with the plasmid pAG1; S—susceptible, embryos transformed with the expression cassette pAG1/promotor-Gmhsp_BRS133; R—resistant, embryos transformed with the expression cassette pAG1/promotorGmhspJF7027.
Figure 19:
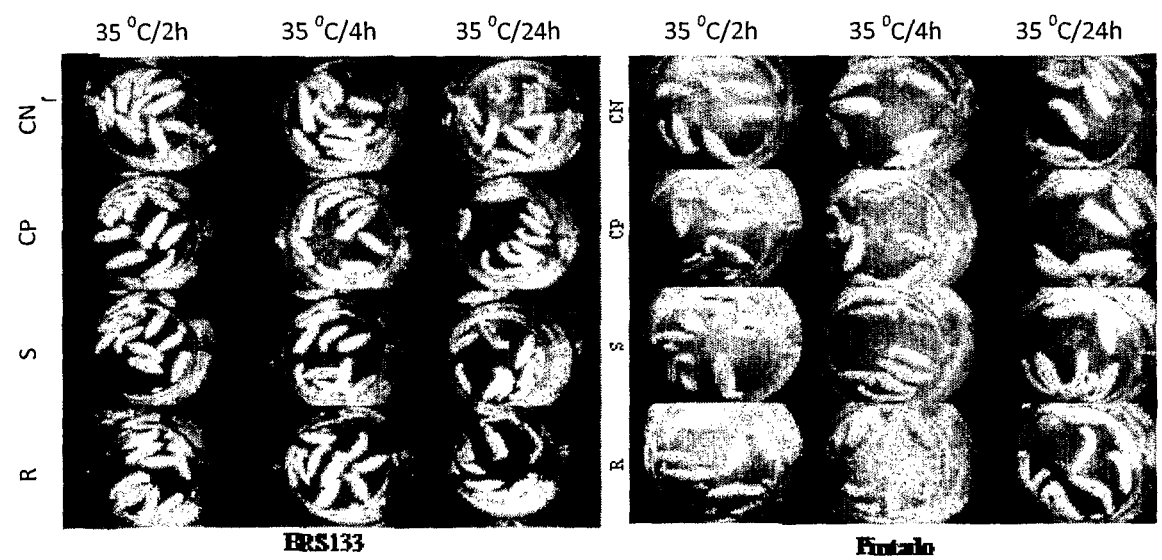
FIG. 19 shows the histochemical test performed with embryos of soybean cultivars BRS133 and Pintado (speckled), susceptible to the cyst nematode M. javanica, transformed, by biobalistics, with expression the cassettes pAG1/promotorGmhsp_BRS133 and pAG1/promotorGmhsp_JF7027, and submitted to heat stress at a temperature of 35° C., for periods of 2 h, 4 h and 24 h. Blue dots indicate positive reaction. CN—negative control, embryos not transformed; CP—positive control, embryos transformed with the plasmid pAG1; S—susceptible, embryos transformed with the expression cassette pAG1/promotor-Gmhsp_BRS133; R—resistant, embryos transformed with the expression cassette pAG1/promotorGmhspJF7027.
Figure 20:
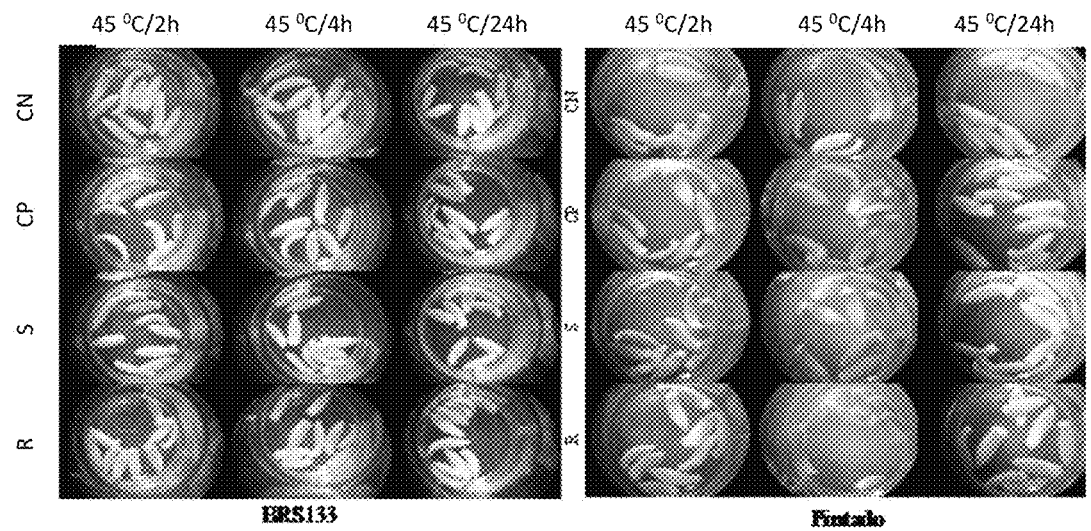
FIG. 20 shows a histochemical test performed with embryos of soybean cultivars BRS133 and Pintado (speckled), susceptible to the cyst nematode M. javanica, transformed, by biobalistics, with the expression cassettes pAG1/promotorGmhsp_BRS133 and pAG1/promotorGmhsp-JF7027, and submitted to heat stress at a temperature of 45° C., for periods of 2 h, 4 h and 24 h. Blue dots indicate positive reaction. CN—negative control, embryos not transformed; CP—positive control, embryos transformed with the plasmid pAG1; S—susceptible, embryos transformed with the expression cassette pAG1/promotor-GmhspBRS133; R—resistant, embryos transformed with the expression cassette pAG1/promotorGmhsp_JF7027.
Figure 21:
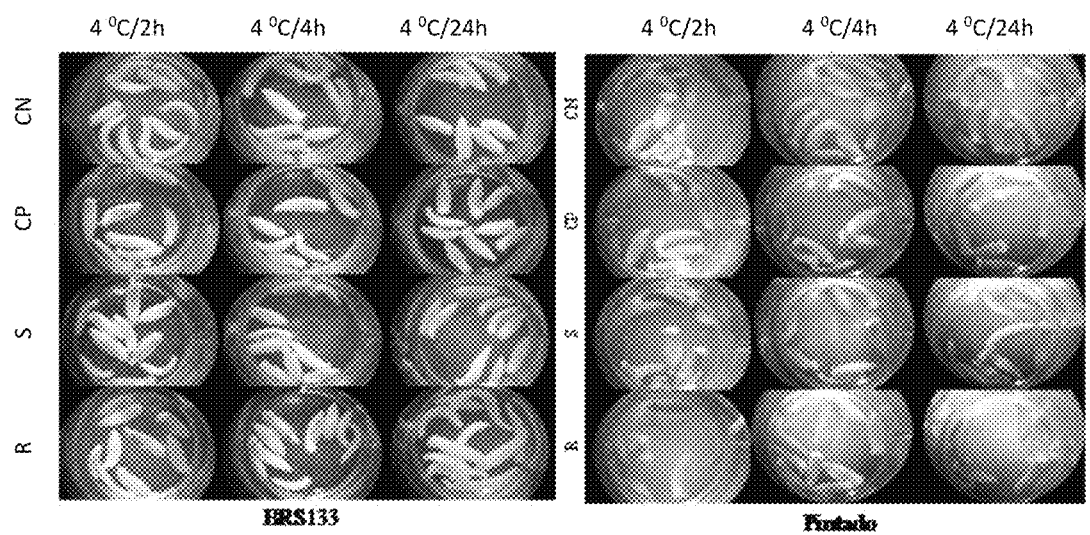
FIG. 21 shows a histochemical test performed with embryos of soybean cultivars BRS133 and Pintado (speckled), susceptible to the cyst nematode M. javanica, transformed, by biobalistics, with the expression cassettes pAG1/promotorGmhspBRS133 and pAG1/promotorGmhsp-JF7027, and submitted to heat stress at a temperature of 4° C., in a refrigerator, for periods of 2 h, 4 h and 24 h. Blue dots indicate positive reaction. CN—negative control, embryos not transformed; CP—positive control, embryos transformed with the plasmid pAG1; S—susceptible, embryos transformed with the expression cassette pAG1/promotorGmhsp_BRS133; R—resistant, embryos transformed with the expression cassette pAG1/promotor-Gmhsp_JF7027.
Figure 22:
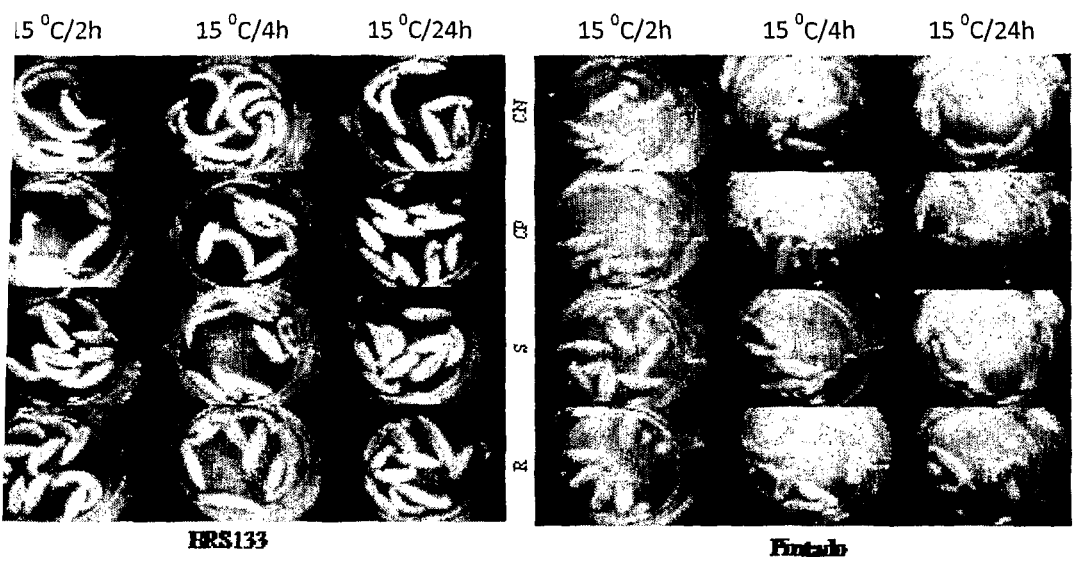
FIG. 22 shows a histochemical test performed with embryos of soybean cultivars BRS133 and Pintado (speckled), susceptible to the cyst nematode M. javanica, transformed, by biobalistics, with the expression cassettes pAG1/promotorGmhspBRS133 and pAG1/promotorGmhsp-JF7027, and submitted to heat stress at a temperature of 15° C., for periods of 2 h, 4 h and 24 h. Blue dots indicate positive reaction. CN—negative control, embryos not transformed; CP—positive control, embryos transformed with the plasmid pAG1; S—susceptible, embryos transformed with the expression cassette pAG1/promotor-GmhspBRS133; R—resistant, embryos transformed with the expression cassette pAG1/promotorGmhsp_JF7027.
Figure 23:
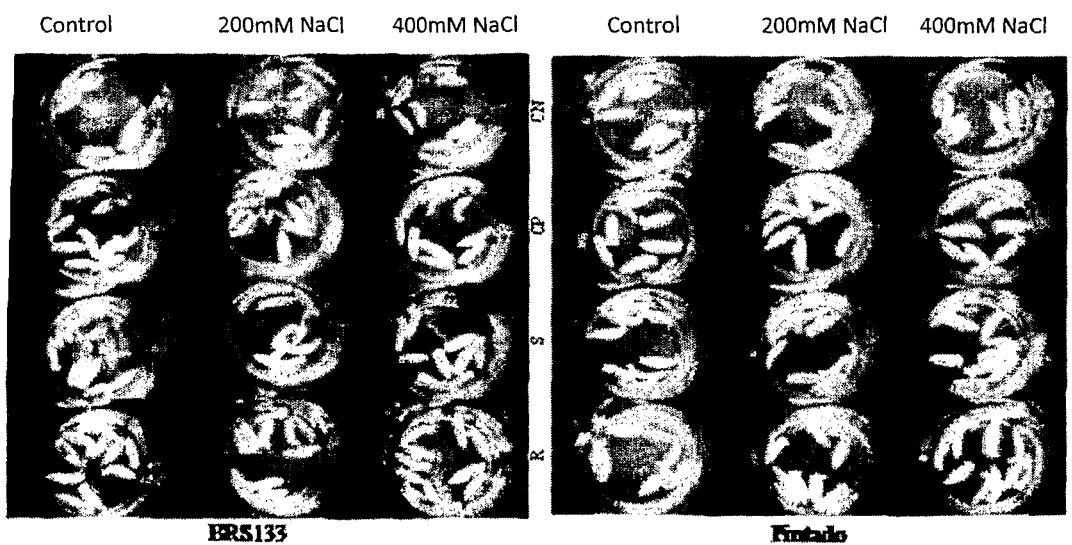
FIG. 23 shows a histochemical test performed with embryos of soybean cultivars BRS133 and Pintado (speckled), susceptible to the cyst nematode M. javanica, transformed, by biobalistics, with the expression cassettes pAG1/promotorGmhspBRS133 and pAG1/promotor'Gmhsp_JF7027, and submitted to salinity stress, concentrations 200 mM, 400 mM of NaCl, for a period of 24 h. Blue dots indicate positive reaction. ON—negative control, embryos not transformed; CP—positive control, embryos transformed with the plasmid pAG1; S—susceptible, embryos transformed with the expression cassette pAG1/promotor-GmhspBRS133; R—resistant, embryos transformed with the expression cassette pAG1/promotorGmhsp_JF7027.
Figure 24:
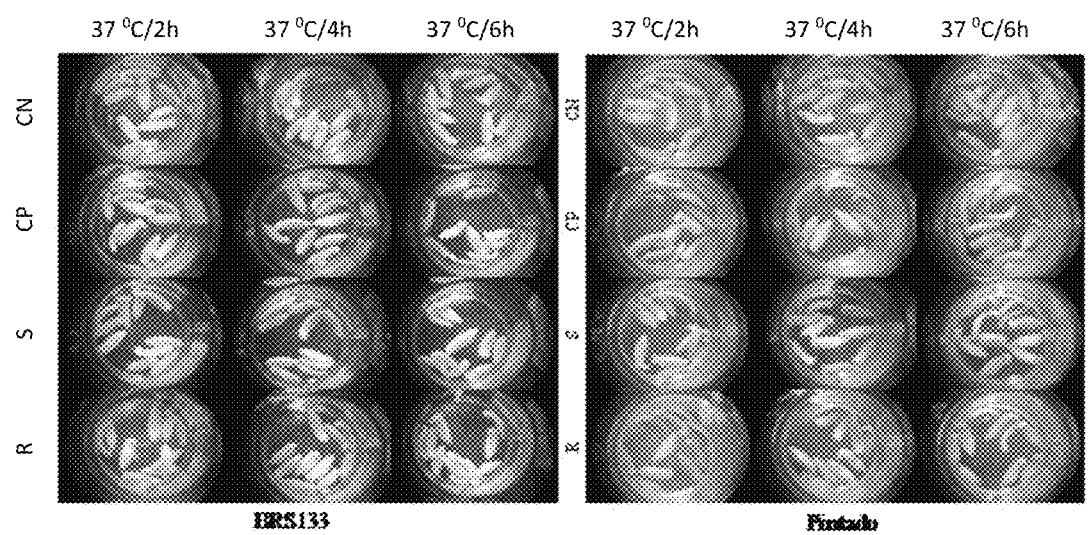
FIG. 24 shows a histochemical test performed with embryos of soybean cultivars BRS133 and Pintado (speckled), susceptible to the cyst nematode M. javanica, transformed, by biobalistics, with the expression cassettes pAG1/promotorGMhsp_BRS133 and pAG1/promotorGmhsp_JF7027, and submitted to drought stress, keeping the embryos in paper filter at 37° C., in a hothouse, for periods of 2 h, 4 h and 6 h. Blue dots indicate positive reaction. CN—negative control, embryos not transformed; CP—positive control, embryos transformed with the plasmid pAG1; S—susceptible, embryos transformed with the expression cassette pAG1/promotorGMhsp_BRS133; R—resistant, embryos transformed with the expression cassette pAG1/promotorGMhspJF7027.
Figure 25:
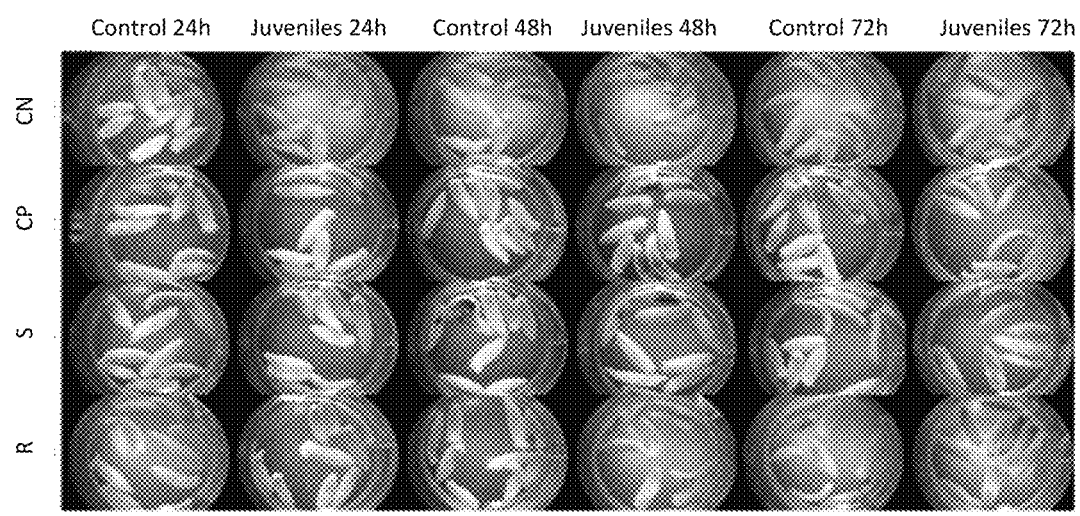
FIG. 25 shows a histochemical test performed with embryos of soybean cultivars BRS133, susceptible to the cyst nematode M. javanica, transformed, by biobalistics, with the expression cassettes pAG1/promotor-GMhsp_BRS133 and pAG1/promotorGmhsp_JF7027, and submitted to biotic stress, with inoculation of 2000 to 3000 J2 per mL. The samples were kept in contact with the pathogen for periods of 24 h, 48 h and 72 h. Blue dots indicate positive reaction. CN—negative control, embryos not transformed; CP—positive control, embryos transformed with the plasmid pAG1; S—susceptible, embryos transformed with the expression cassette pAG1/promotor-GMhsp_BRS133; R—resistant, embryos transformed with the expression cassette pAG1/promotorGMhspJF7027.
Figure 26:
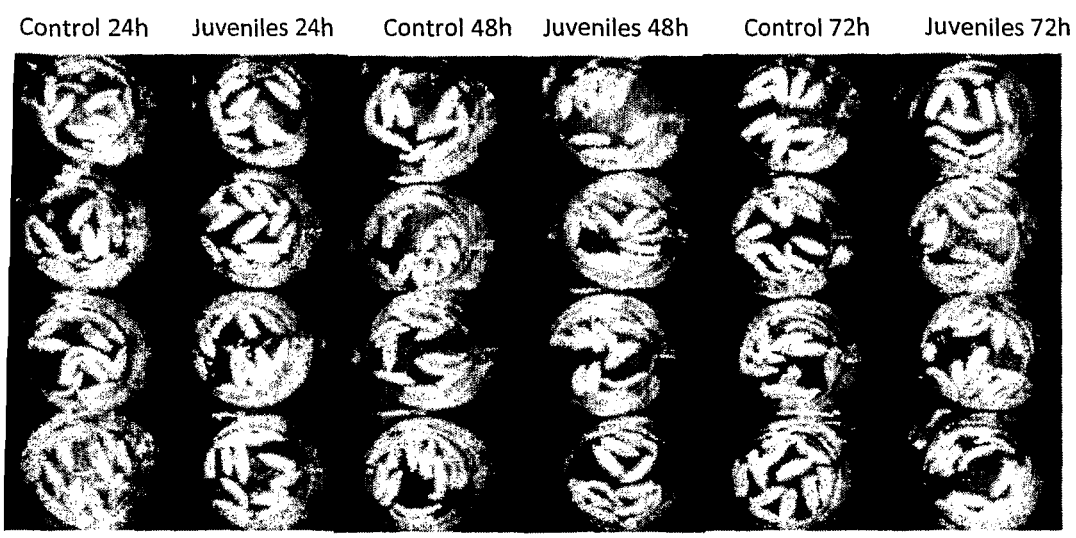
FIG. 26 shows a histochemical test performed with embryos of soybean cultivars Pintado (speckled), susceptible to the cyst nematode M. javanica, transformed, by biobalistics, with the expression cassettes pAG1/promotor-GmhspBRS133 and pAG1/promotorGmhsp_JF7027, and submitted to biotic stress, with inoculation of 2000 to 3000 J3 per mL. The samples were kept in contact with the pathogen for periods of 24 h, 48 h and 72 h. Blue dots indicate positive reaction. CN—negative control, embryos not transformed; CP—positive control, embryos transformed with the plasmid pAG1; S—susceptible, embryos transformed with the expression cassette pAG1/promotor-Gmhsp_BRS133; R—resistant, embryos transformed with the expression cassette pAG1/promotorGmhsp_JF7027.

Histochemical Assay in Embryos Transformed With Different Expression Cassettes and Submitted to Different Stresses The expression product of the Gus gene can be used as a marker reporter of selection by detecting its enzymatic activity in plant tissues through histochemical assays. This qualitative method is based on the cleavage of the 5-bromo-4-chloro-3-indolyl-b-D-glucuronide (X-gluc) substrate, by the b-glucuronidase enzyme, generating, in the presence of oxygen, dimers that result in an insoluble blue precipitate. This methodology auxiliates gene expression regulation studies regarding tissue specificity, the isolation of promoters, the identification of transgenic plants and the optimization of transfer conditions (Brasileiro (1998), In: Brasileiro, A.C.M.; Carneiro, V.T.C. (ed.). Manual de transformagão genética de plantas. Brasília: Embrapa—SPI/Embrapa-Cenargen, 1998, p. 143-154; Aragao et al. (2000), Theor. Appl. Gen, 101:1-6). This way, embryos of both genotypes, BRS133 and Pintado, transformed with different cassettes, after being submitted to different stresses, were transferred to plates and the X-Gluc reaction buffer was added in enough volume to cover the samples. This buffer was prepared by diluting 8.5 mg of X-Gluc in 85 mL of dimetilformamide. Phosphate buffer (NaH2PO4—50 mM pH 7.0) was added to the volume of 17 mL and, at last, 17 mL of Triton X-100. The solution, after preparation, was stored in refrigerator. The plate containing embryos and buffer was sealed and incubated in the dark in hothouse at 37° C., for approximately 16 h. Following, the buffer was removed and 1 mL of 70% ethanol was added to stop the reaction. The samples were analyzed under a stereomicroscope, model SQZ-DS4-BI (Tecnival), and images were acquired to document the results. Histochemical assay results, after submission to stress, indicate that the cultivar BRS133 present stronger responses when the reagent X-Gluc is performed, since blue spots are visible in an obvious fashion and in restricted areas that represent cells that were transformed. This insoluble blue precipitate is the product of the Gus gene reaction present in the construct cassette, which coded for the β—glucuronidase, which reacts with the X-Gluc substrate, which in the presence of O2, forms dimmers that precipitate. When the embryo assay results from the cultivar Pintado were analyzed, in most of the stresses, positive blue spots were not detected. In this cultivar, the endogenous GUS expression was higher, resulting in a completely blue embryo, a result which interferes in the analysis. Background endogenous GUS activity in soybean embryos were reported in previous studies. Hu and collaborators (Plant Cell Reports, 9: 1-5, 1990) analyzed 52 different plant species, testing intrinsic GUS activity in leaves, fruit parts, seeds and embryos. In this study, soybean presented, in mature embryos from fresh fruits and mature embryos of dehydrated seeds, strong positive staining, result of the endogenous GUS activity. This way, the heat stress was applied by submitting transgenic embryos to temperatures of 25° C., 35° C. and 45° C., in hothouse, for periods of 2 h, 4 h and 24 h. FIGS. 18, 19 and 20 show, respectively, these treatments for both tested cultivars. The cold stress was applied by submitting transgenic embryos to temperatures of 4° C. and 15° C., in refrigerator and hothouse for periods of 2 h, 4 h and 24 h (FIGS. 21 and 22). For this stress, the difference observed between the cultivars regarding the histochemical reaction positive blue spots was much more pronounced in Pintado embryos, being constitutively blue, and results from the endogenous GUS activity, previously described in the literature (Hu at al. (1990), Plant Cell Reports, 9: 1-5). Once again, the embryos from the cultivar BRS133 presented a better response to the histochemical assay indicating that this cultivar must be the chosen one and used in future steps of the study. The salinity stress experiment was performed by maintaining the transgenic embryos in water as a control and in concentration of NaCl of 200 mM, 400 mM for a period of 24 h. The embryos from the cultivar BRS133 continue to respond positively to the assay, presenting blue spots in restricted areas, and, differently from the previous stresses, the cultivar Pintado did not present obvious or detectable response. FIG. 23 presents the results. The drought stress was applied by placing the embryos in filter paper at 37° C., keeping them in hothouse for periods of 2 h, 4 h and 6 h. Once again, the cultivar BRS133 presented positive response to the histochemical assay, while the cultivar Pintado presented again negative response, with inespecific blue staining of embryos as a result of the endogenous GUS expression, as shown in FIG. 24. The infection of embryos from cultivars BRS133 and Pintado using juvenile J2, which is the infecting phase of the gall nematode *M. javanica*, constituted the biotic stress. Approximately 2000 to 3000 J2 per mL were incubated with the transgenic samples and maintained for periods of 24 h, 48 h and 72 h. The results demonstrate that the cultivar BRS133 (FIG. 25) presented positive blue spots from the histochemical assay, indicating that the cassette expression occurred in satisfactory fashion. As the time went by, the embryos have theirs aspect modified, presenting a red-brownish color, including, the control samples. This change, more visible after 72 h, can be caused by the attack of embryos by the infecting form of the nematode that, at the time of infection, injects hormones and substances, which enables cell modifications, in the same fashion that occurs in roots of host plants. However, the embryos named R, transformed with the resistant expression cassette, pAG1/promotorGmhsp_JF7027, had their aspect less affected, and the sample inoculated at 72 h maintained its original aspect, which is a white color, suggesting that, somehow, the cassette containing the promoter region of the Gmhsp17.6-L gene from the individual from the resistant population JF7027, with the higher number of AT(n) repeats, present a better response to the pathogen attack, maybe, due to the higher expression level of chaperone. The embryos from the Pintado, when submitted to biotic stress by inoculation of J2 nematode also presented, besides de negative response to the histochemical assay, being constitutively blue-stained, the response of change of color, more pronounced from the 48 h period and, especially at 72 h. FIG. 26 presents the results.

It can be concluded from the presented results for the cultivars BRS133 and Pintado, after the submission to the biotic and abiotic stresses, that the histochemical assay detected the presence of the marker gene Gus, however, high endogenous activity was also observed, especially, in the cultivar Pintado, suggesting that different materials presented distinct responses to the transformation process.

It is worth mentioning that the Gus expression is considered just as an evidence of transformation, being insufficient as definitive proof of integration of the Gus gene to the plant genome (Potrykus (1990), Physiologia Plantarum 79: 129-134). The definitive proof of integration of any exogenous DNA sequence is provided by genomic DNA hybridization using specific probes, through molecular biology techniques.

---

The invention claimed is:

1. A method for regulating expression levels of coding sequences in plants comprising:
   (i) stably transforming a plant cell with an expression cassette comprising a modified promoter element operably linked to a coding sequence of interest,
   wherein said modified promoter element is a variant of an unmodified promoter element, said unmodified promoter element having the nucleotide sequence of SEQ ID NO: 21, and wherein said modified promoter element contains between 9 and 33 AT repetitions between the nucleotide positions that correspond to nucleotide positions 114 to 132 of SEQ ID NO: 21;
   (ii) culturing the stably transformed plant cell under plant cell growing conditions; and
   (iii) regenerating a transgenic plant having stably incorporated into its genome the cassette of (i).

2. The method according to claim 1, wherein said method is used for the control of nematodes in plants.

3. The method of claim 2, wherein the nematode is the gall nematode *Meloidogyne javanica*.

4. An expression cassette comprising a modified promoter element operably linked to a heterologous sequence,
   wherein said modified promoter element is a variant of an unmodified promoter element, said unmodified promoter element having the nucleotide sequence of SEQ ID NO: 21, and wherein said modified promoter element contains between 9 and 33 AT repetitions between the nucleotide positions that correspond to nucleotide positions 114 to 132 of SEQ ID NO: 21.

5. The expression cassette of claim 4, wherein said expression cassette is suitable for transforming soybean embryos.

6. The expression cassette of claim 4, wherein said expression cassette is used to control nematodes in plants.

7. The expression cassette of claim 6, wherein the nematode is the gall nematode *Meloidogyne javanica*.

8. A process for obtaining genetically modified plants comprising a modified promoter element, wherein said method comprises:
   (i) stably transforming a plant cell with an expression cassette comprising a modified promoter element operably linked to a coding sequence,
   wherein said modified promoter element is a variant of an unmodified promoter element, said unmodified promoter element having the nucleotide sequence of SEQ ID NO: 21, and wherein said modified promoter element contains between 9 and 33 AT repetitions between the nucleotide positions that correspond to nucleotide positions 114 to 132 of SEQ ID NO: 21;
   (ii) culturing the stably transformed plant cell under plant cell growing conditions; and
   (iii) regenerating a stably genetically modified plant.

9. The process according to claim 8, wherein the coding sequence operably linked to the modified promoter element is over-expressed.

10. The process according to claim 8, wherein the coding sequence operably linked to the modified promoter element is under-expressed.

11. The process according to claim 8, wherein said plants are resistant to a nematode.

12. The process of claim 11, wherein said nematode is the gall nematode *Meloidogyne javanica*.

13. The method according to claim 1, wherein the expression vector is derived from a pAG1 vector.

* * * * *

SEQUENCE LISTING

```
<160> NUMBER OF SEQ ID NOS: 28

<210> SEQ ID NO 1
<211> LENGTH: 10
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (5)..(6)
<223> OTHER INFORMATION: n is a, c, g, or t

<400> SEQUENCE: 1 agaannttct                                                            10
```

<210> SEQ ID NO 2
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 2
cttctagaag cttctagaag                                              20

<210> SEQ ID NO 3
<211> LENGTH: 14
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 3
ctngaanntt cnag                                                    14

<210> SEQ ID NO 4
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 4
caccgcggtg gaattctgaa attgggtctt tttg                              34

<210> SEQ ID NO 5
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 5
ccatggaatg gggacactcg aggtatt                                      27

<210> SEQ ID NO 6
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 6
gggctgcagg aattctgaaa ttgggtcttt ttg                               33

<210> SEQ ID NO 7
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 7 cccccccgggt taaccagaga tttctatagc ct                                    32

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
gacatcatca aacaagagaa                                                   20

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 9
tctctccgct aatctgaa                                                     18

<210> SEQ ID NO 10
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 10
gctgtgtgtc attgtcatcg aa                                                22

<210> SEQ ID NO 11
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 11
cacggtctat ttcttgccta catc                                              24

<210> SEQ ID NO 12
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 12
gggctgcagg aattctgaaa ttgggtcttt ttg                                    33

<210> SEQ ID NO 13
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 13
cccggatcca atggggacac tcgaggtatt                                        30

<210> SEQ ID NO 14
<211> LENGTH: 20

```
<212> TYPE: DNA
<213> ORGANISM: Artificial Sequence
<220> FEATURE:
<223> OTHER INFORMATION: Synthetic polynucleotide

<400> SEQUENCE: 14
actagagatt ccagcgtcac                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
gtggctatac agatacctgg                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
gaatcctgtt gccggtcttg                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
ttatcctagt ttgcgcgcta                                                 20

<210> SEQ ID NO 18
<211> LENGTH: 1711
<212> TYPE: DNA
<213> ORGANISM: Artificial Sequence
<220> FEATURE:
<223> OTHER INFORMATION: Synthetic polynucleotide

<400> SEQUENCE: 18
gaattctgaa attgggtctt tttgtgggca cttttttgatg tttttgttta agttactgta      60
ctgtgggcca caaacgtat agatcaaagt agtaataata atattgatta aatgatatat       120
atatatatat atatatatat atatctagaa ggttgtagaa gactagctag aacgtacgta     180
ttcgtgtgga gaagtcctga agtttatcga atcatctaaa actgctaaaa tagcaaacaa     240
cattatattg taaacaatat ttttctggaa catacaagag tatcctttca cttcctttaa     300
atacctcgag tgtccccatt gacatcatca aacaagagaa gagttacaga atttcctgtt     360
tacgatctca ttacaatttt gcaactttca aagcttatta gctaaagtaa catcaaaaga     420
tgtcattgat tccaagtatt ttcggtggcc caaggagcaa cgtgttcgat ccattctcac     480
tcgatatgtg ggatcccttc aaggattttc atgttcccac ttcttctgtt tctgctgaaa     540
attctgcatt tgtgaacaca cgtgtggatt ggaaggagac ccaagaggca cacgtgctca     600
aggctgatat tccagggctg aagaaagagg aagtgaaggt tcagattgaa gatgataggg     660
ttcttcagat tagcgcgagag aggaacgttg agaaggaaga caagaacgac acgtggcatc     720
```

```
gcgtggaccg tagcagtgga aagttcatga gaaggttcag attgccagag aatgcaaaag    780
tggagcaagt aaaggcttgt atggaaaatg gggttctcac tgttactatt ccaaaggaag    840
aggttaagaa gtctgatgtt aagcctatag aaatctctgg ttaaacttgg tttcactgaa    900
aatcgtgaga gcttttaaat ttgctttgtt gtaataagtg tcctttgtct tgtgttccaa    960
tggtgatttt gagaaagatc atacaattgt gccttgtgtt gttgtgcaag tgtaattgaa   1020
gtgaataaaa aattaacacc tgctttcaga aaattttgct gtgtgtcatt gtcatcgaat   1080
atgtgatgta ggcaagaaat agaccgtgaa ataatatct gacatttggc taattgcttt    1140
tgttatgctg agacactcta tgtgaaataa ctgcatttat catgttccat cttcttaata   1200
caagaagtca ataccaatgt cttaccaaat taagataaca ggttgatttg gactcatcaa   1260
agtgcagccc tttatttgga ctcatcaaag tgcagcacta aagggttttg ttaactagca   1320
agttcagagc atcatttaag taattaaaag aaaaaatatt aaatatataa atcataagat   1380
gatatcaaaa aattcatgaa cagtctcttc attttttttc aataaaaata ttttttatttt   1440 aattttttaa aataatatcc tcataacatt ggtttaactc ccaagtttaa aatttactag   1500
tgctagataa attctctaag ataatgtata gataaaaata agataaatta gaaaattttt   1560
aaggagagat ttttttttat aaaaattagg tatatgtatt ggttttagtt tacagagaaa   1620
tataatttat attttctttt tgtgtaaata ttaatgaaaa aaattattca aattcaattc   1680
taaatcttaa tatttttttt gacagaattc t                                  1711

<210> SEQ ID NO 19
<211> LENGTH: 311
<212> TYPE: DNA
<213> ORGANISM: Artificial Sequence
<220> FEATURE:
<223> OTHER INFORMATION: Synthetic polynucleotide

<400> SEQUENCE: 19
gaattctgaa attgggtctt tttgtgggca cttttttgatg tttttgttta agttactgta     60
ctgtgggcca caaaacgtat agatcaaagt agtaataata atattgatta aatgatatat    120
acatatatat atctagaagg ttgtagaaga ctagctagaa cgtacgtatt cgtgtggaga    180
agtcctgaag tttatcgaat catctaaaac tgctaaaata gcaaacaaca ttatattgta    240
aacaatattt ttctggaaca tacaagagta tcctttcact tcctttaaat acctcgagtg    300
tccccattga c                                                         311

<210> SEQ ID NO 20
<211> LENGTH: 355
<212> TYPE: DNA
<213> ORGANISM: Artificial Sequence
<220> FEATURE:
<223> OTHER INFORMATION: Synthetic polynucleotide

<400> SEQUENCE: 20
gaattctgaa attgggtctt tttgtgggca cttttttgatg tttttgttta agttactgta     60
ctgtgggcca caaaacgtat agatcaaagt agtaataata atattgatta aatgatatat    120
atatatatat atatatatat atatatatat atatatatat atatatatat atatatctag    180
aaggttgtag aagactagct agaacgtacg tattcgtgtg gagaagtcct gaagtttatc    240
gaatcatcta aaactgctaa aatagcaaac aacattatat tgtaaacaat atttttctgg    300
aacatacaag agtatccttt cacttccttt aaatacctcg agtgtcccca ttgac         355
```

<210> SEQ ID NO 21
<211> LENGTH: 311
<212> TYPE: DNA
<213> ORGANISM: Artificial Sequence
<220> FEATURE:
<223> OTHER INFORMATION: Synthetic polynucleotide

<400> SEQUENCE: 21

| gaattctgaa attgggtctt tttgtgggca cttttttgatg tttttgttta agttactgta | 60 |
| ctgtgggcca caaaacgtat agatcaaagt agtaataata atattgatta aatgatatat | 120 |
| atatatatat atctagaagg ttgtagaaga ctagctagaa cgtacgtatt cgtgtggaga | 180 |
| agtcctgaag tttatcgaat catctaaaac tgctaaaata gcaaacaaca ttatattgta | 240 |
| aacaatattt ttctggaaca tacaagagta tcctttcact tcctttaaat acctcgagtg | 300 |
| tccccattga c | 311 |

<210> SEQ ID NO 22
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 22

| gaattctgaa attgggtctt tttgtgggca cttttttgatg tttttgttta agttactgta | 60 |
| ctgtgggcca caaaacgtat agatcaaagt agtaataata atattgatta aatgatatat | 120 |
| atatatatat atatatatat atatatatat atatatatat atatatatat atatatatat | 180 |
| atatctagaa ggttgtagaa gactagctag aacgtacgta ttcgtgtgga gaagtcctga | 240 |
| agtttatcga atcatctaaa actgctaaaa tagcaaacaa cattatattg taaacaatat | 300 |
| ttttctggaa catacaagag tatcctttca cttcctttaa atacctcgag tgtccccatt | 360 |
| gac | 363 |

<210> SEQ ID NO 23
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 23

| gaattctgaa attgggtctt tttgtgggca cttttttgatg tttttgttta agttactgta | 60 |
| ctgtgggcca caaaacgtat agatcaaagt agtaataata atattgatta aatgatatat | 120 |
| atatatatat atatatatat atatatatat atatatatat atatatatat atatatatct | 180 |
| agaaggttgt agaagactag ctagaacgta cgtattcgtg tggagaagtc ctgaagttta | 240 |
| tcgaatcatc taaaactgct aaaatagcaa acaacattat attgtaaaca atatttttct | 300 |
| ggaacataca agagtatcct ttcacttcct ttaaatacct cgagtgtccc cattgac | 357 |

<210> SEQ ID NO 24
<211> LENGTH: 353
<212> TYPE: DNA
<213> ORGANISM: Artificial Sequence
<220> FEATURE:
<223> OTHER INFORMATION: Synthetic polynucleotide

<400> SEQUENCE: 24

| gaattctgaa attgggtctt tttgtgggca cttttttgatg tttttgttta agttactgta | 60 |

| | | |
|---|---|---|
| ctgtgggcca caaaacgtat agatcaaagt agtaataata atattgatta aatgatatat | 120 | |
| atatatatat atatatatat atatatatat atatatatat atatatatat atatctagaa | 180 | |
| ggttgtagaa gactagctag aacgtacgta ttcgtgtgga gaagtcctga agtttatcga | 240 | |
| atcatctaaa actgctaaaa tagcaaacaa cattatattg taaacaatat ttttctggaa | 300 | |
| catacaagag tatcctttca cttcctttaa atacctcgag tgtccccatt gac | 353 | |

<210> SEQ ID NO 25
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 25

| | |
|---|---|
| atcatcaaac aagagaagag ttacagaatt tcctgtttac gatctcatta caattttgca | 60 |
| actttcaaag cttattagct aaagtaacat caaaagatg | 99 |

<210> SEQ ID NO 26
<211> LENGTH: 465
<212> TYPE: DNA
<213> ORGANISM: Artificial Sequence
<220> FEATURE:
<223> OTHER INFORMATION: Synthetic polynucleotide

<400> SEQUENCE: 26

| | |
|---|---|
| atgtcattga ttccaagtat tttcggtggc ccaaggagca acgtgttcga tccattctca | 60 |
| ctcgatatgt gggatccctt caaggatttt catgttccca cttcttctgt ttctgctgaa | 120 |
| aattctgcat tgtgaacac acgtgtggat tggaaggaga cccaagaggc acacgtgctc | 180 |
| aaggctgata ttccagggct gaagaaagag gaagtgaagg ttcagattga agatgatagg | 240 |
| gttcttcaga ttagcggaga gaggaacgtt gagaaggaag acaagaacga cacgtggcat | 300 |
| cgcgtggacc gtagcagtgg aaagttcatg agaaggttca gattgccaga gaatgcaaaa | 360 |
| gtggagcaag taaaggcttg tatggaaaat ggggttctca ctgttactat tccaaggaa | 420 |
| gaggttaaga gtctgatgt taagcctata gaaatctctg gttaa | 465 |

<210> SEQ ID NO 27
<211> LENGTH: 154
<212> TYPE: PRT
<213> ORGANISM: Artificial Sequence
<220> FEATURE:
<223> OTHER INFORMATION: Synthetic polypeptide

<400> SEQUENCE: 27

Met Ser Leu Ile Pro Ser Ile Phe Gly Gly Pro Arg Ser Asn Val Phe
1               5                   10                  15

Asp Pro Phe Ser Leu Asp Met Trp Asp Pro Phe Lys Asp Phe His Val
            20                  25                  30

Pro Thr Ser Ser Val Ser Ala Glu Asn Ser Ala Phe Val Asn Thr Arg
        35                  40                  45

Val Asp Trp Lys Glu Thr Gln Glu Ala His Val Leu Lys Ala Asp Ile
    50                  55                  60

Pro Gly Leu Lys Lys Glu Val Lys Val Gln Ile Glu Asp Asp Arg
65                  70                  75                  80

Val Leu Gln Ile Ser Gly Glu Arg Asn Val Glu Lys Glu Asp Lys Asn
                85                  90                  95

Asp Thr Trp His Arg Val Asp Arg Ser Ser Gly Lys Phe Met Arg Arg

-continued

```
               100                 105                 110
Phe Arg Leu Pro Glu Asn Ala Lys Val Glu Gln Val Lys Ala Cys Met
        115                 120                 125

Glu Asn Gly Val Leu Thr Val Thr Ile Pro Lys Glu Glu Val Lys Lys
    130                 135                 140

Ser Asp Val Lys Pro Ile Glu Ile Ser Gly
145                 150

<210> SEQ ID NO 28
<211> LENGTH: 99
<212> TYPE: DNA
<213> ORGANISM: Artificial Sequence
<220> FEATURE:
<223> OTHER INFORMATION: Synthetic polynucleotide

<400> SEQUENCE: 28
atcatcaaac aagagaagag ttacagaatt tcctgtttac gatcttattg caattttgca      60
actttcaaag cttattagct aaagtaacat caaaagatg                            99
```